US008944819B2

(12) United States Patent
Faasse et al.

(10) Patent No.: US 8,944,819 B2
(45) Date of Patent: *Feb. 3, 2015

(54) DEVICE AND METHOD FOR DELIVERING AN ORAL CARE AGENT

(75) Inventors: Adrian L. Faasse, Carmel Valley, CA (US); Steven Richard Klemm, Grand Rapids, MI (US); Glen Edward Groeneweg, Lowell, MI (US); Alan Gene Thelen, Sunfield, MI (US)

(73) Assignee: Ranir, LLC, Grand Rapids, MI (US)

( * ) Notice: Subject to any disclaimer, the term of this patent is extended or adjusted under 35 U.S.C. 154(b) by 369 days.
This patent is subject to a terminal disclaimer.

(21) Appl. No.: 12/974,627

(22) Filed: Dec. 21, 2010

(65) Prior Publication Data
US 2011/0086329 A1 Apr. 14, 2011

Related U.S. Application Data

(63) Continuation of application No. 10/985,709, filed on Nov. 10, 2004.

(51) Int. Cl.
*A61Q 11/00* (2006.01)
*A61C 19/06* (2006.01)
*A61K 6/00* (2006.01)
*A61K 8/00* (2006.01)

(52) U.S. Cl.
CPC .................................. *A61C 19/063* (2013.01)
USPC ........ 433/215; 433/216; 433/217.1; 424/401; 424/49; 424/53

(58) Field of Classification Search
USPC ..................... 433/215, 216, 217.1; 424/49, 53
See application file for complete search history.

(56) References Cited

U.S. PATENT DOCUMENTS

| | | | |
|---|---|---|---|
| 3,416,527 A | 12/1968 | Hoef | 128/260 |
| 3,527,219 A | 9/1970 | Greenberg | 128/260 |
| 4,173,219 A | 11/1979 | Lentine | 128/136 |
| 4,581,821 A | 4/1986 | Cahalan et al. | 29/877 |
| 4,615,697 A | 10/1986 | Robinson | 604/890 |
| 4,695,464 A | 9/1987 | Alderman | 424/449 |
| 4,713,243 A | 12/1987 | Schiraldi et al. | 424/151 |
| 4,772,470 A | 9/1988 | Inoue et al. | 424/435 |
| 4,792,450 A | 12/1988 | Kydonieus et al. | 424/449 |
| RE33,093 E | 10/1989 | Schiraldi et al. | 424/676 |
| 4,889,720 A | 12/1989 | Konishi | 424/448 |
| 5,032,178 A | 7/1991 | Cornell | 106/35 |
| 5,098,303 A | 3/1992 | Fischer | 433/215 |
| 5,108,742 A | 4/1992 | Merianos | 424/78.32 |
| 5,279,816 A | 1/1994 | Church et al. | 424/53 |
| 5,310,563 A | 5/1994 | Curtis et al. | 424/616 |
| 5,326,685 A | 7/1994 | Gaglio et al. | 433/215 |
| 5,415,544 A | 5/1995 | Oxman et al. | 433/48 |
| 5,438,076 A | 8/1995 | Friedman et al. | 514/772.6 |
| 5,512,293 A | 4/1996 | Landrau et al. | 424/449 |
| 5,575,654 A | 11/1996 | Fontenot | 433/215 |
| 5,599,553 A | 2/1997 | Chung | 424/435 |
| 5,614,223 A | 3/1997 | Sipos | 424/489 |
| 5,626,866 A | 5/1997 | Ebert et al. | 424/447 |
| 5,631,000 A | 5/1997 | Pellico et al. | 424/53 |
| 5,639,795 A | 6/1997 | Friedman et al. | 514/772.6 |
| 5,643,603 A | 7/1997 | Bottenberg et al. | 424/488 |
| 5,648,399 A | 7/1997 | Friedman et al. | 514/772.6 |
| 5,700,478 A | 12/1997 | Biegajski et al. | 424/434 |
| 5,780,045 A | 7/1998 | McQuinn et al. | 424/434 |
| 5,829,979 A | 11/1998 | Kobashigawa et al. | 433/180 |
| 5,851,512 A | 12/1998 | Fischer | 424/49 |
| 5,858,332 A | 1/1999 | Jensen et al. | 424/53 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,921,778 A | 7/1999 | Karmaker et al. | 433/215 |
| 5,928,628 A | 7/1999 | Pellico | 424/49 |
| 5,961,958 A | 10/1999 | Homola et al. | 424/49 |

(Continued)

FOREIGN PATENT DOCUMENTS

| | | | | |
|---|---|---|---|---|
| CA | 2293352 | 12/1998 | | A61K 8/72 |
| CA | 2338331 | 12/2000 | | A61C 19/06 |

(Continued)

OTHER PUBLICATIONS

Gerlach, R. W., et al. "Vital Bleaching with Whitening Strips: Summary of Clinical Research on Effectiveness and Tolerability ," *The Journal of Contemporary Dental Practice*, 2:3, pp. 1-15, (Summer Issue, 2001).
McMillan, D. A., et al. "Impact of Increasing Hydrogen Peroxide Concentration on Bleaching Strip Efficacy and Tolerability," $30^{th}$ *Annual Meeting of the AADR*, 1102 (Mar. 2001).
Harris, M. P., et al. "Effect of Carbamide Peroxide Concentration on Bleaching Efficacy," $30^{th}$ *Annual Meeting of the AADR*, 1096 (Mar. 2001).
Gerlach, R. W., et al. "Use of Peroxide Containing Polyethylene Strips: Effect of Dosing Duration on Initial and Sustained Shade Change," $30^{th}$ *Annual Meeting of the AADR*, 920 ( Mar. 2001).
Sagel, P.A., et al. "Clinical Comparison of Whitening with 6.0% and 5.3% Hydrogen Peroxide Whitening Strips," www.dentalcare.com/soap/journals/pgresrch/posters/iadr02/pp1951.htm (Sep. 17, 2002).
McMillan, D.A., et al. "Peroxide Degradation Kinetics During Use of Crest Whitestrips," www.dentalcare.com/soap/products/research/aadr01/pp1101.htm (Sep. 16, 2002).
Fitzgerald, J. A., et al. "Comparative In Vitro Antimicrobial Activity of Peroxide Gels in Strip or Tray Bleaching Systems," $30^{th}$ *Annual Meeting of the AADR*, 356 (Mar. 2001).
Sagel, P. A., et al. "Vital Tooth Whitening With a Novel Hydrogen Peroxide Strip System: Design, Kinetics, and Clinical Response," *Compendium, Supplement*, 21:29, pp. S10-S15 (2000).
Sagel, P. A., et al. "Overview of a Professional Tooth-Whitening System Containing 6.5% Hydrogen Peroxide Whitening Strips," *Compendium, Special Issue*, 23:1A, pp. 9-15 (2002).

(Continued)

*Primary Examiner* — Lezah Roberts
(74) *Attorney, Agent, or Firm* — Warner Norcross & Judd LLP

(57) ABSTRACT

An oral care agent delivery device is provided which comprises a permanently deformable backing layer, an oral care layer, and a non-woven binding material with a first part that is substantially invested in the oral care layer and a second part that is substantially invested in the backing layer. The device is sized to fit over a plurality of teeth in an upper or lower dental arch of a subject. The oral care layer comprises at least one oral care agent and at least one hydrophilic polymer. When hydrated, the oral care layer has an adhesiveness relative to the surface of a user's teeth that is sufficient to retain the device on the user's teeth when placed thereon. The device can also have an oral care agent which is activated on hydration of the oral care layer, or an oral care layer which releases the oral care agent over time.

39 Claims, 3 Drawing Sheets

(56) References Cited

U.S. PATENT DOCUMENTS

| | | | |
|---|---|---|---|
| 5,980,249 A | 11/1999 | Fontenot et al. | 433/80 |
| 5,985,249 A | 11/1999 | Fischer | 424/49 |
| 5,989,569 A | 11/1999 | Dirksing et al. | 424/401 |
| 6,004,538 A | 12/1999 | Hughes et al. | 424/49 |
| 6,004,582 A | 12/1999 | Faour et al. | 424/473 |
| 6,036,943 A | 3/2000 | Fischer | 424/49 |
| 6,045,811 A | 4/2000 | Dirksing et al. | 424/401 |
| 6,074,719 A | 6/2000 | Fukushi et al. | 428/36.9 |
| 6,096,328 A | 8/2000 | Sagel et al. | 424/401 |
| 6,136,297 A | 10/2000 | Sagel et al. | 424/49 |
| 6,197,331 B1 | 3/2001 | Lerner et al. | 424/448 |
| 6,247,930 B1 | 6/2001 | Chiang et al. | 433/215 |
| 6,274,122 B1 | 8/2001 | McLaughlin et al. | 424/53 |
| 6,287,120 B1 | 9/2001 | Wiesel | 433/215 |
| 6,312,671 B1 | 11/2001 | Jensen et al. | 424/53 |
| 6,325,993 B1 | 12/2001 | Saito et al. | 424/49 |
| 6,326,022 B1 | 12/2001 | Katz | 424/435 |
| 6,331,292 B1 | 12/2001 | Montgomery | 424/53 |
| 6,343,932 B1 | 2/2002 | Wiesel | 433/215 |
| 6,350,438 B1 | 2/2002 | Witt et al. | 424/53 |
| 6,358,525 B1 | 3/2002 | Guo et al. | 424/464 |
| 6,375,963 B1 | 4/2002 | Repka et al. | 424/402 |
| 6,419,906 B1 | 7/2002 | Xu et al. | 424/53 |
| 6,448,323 B1 | 9/2002 | Jordan et al. | 524/451 |
| 6,464,961 B2 | 10/2002 | Plochocka | 424/49 |
| 6,488,914 B2 | 12/2002 | Montgomery | 424/53 |
| 6,500,408 B2 | 12/2002 | Chen et al. | 424/530 |
| 6,503,486 B2 | 1/2003 | Xu et al. | 424/53 |
| 6,506,053 B2 | 1/2003 | Wiesel | 433/215 |
| 6,514,483 B2 | 2/2003 | Xu et al. | 424/53 |
| 6,514,484 B2 | 2/2003 | Rajaiah et al. | 424/53 |
| 6,551,579 B2 | 4/2003 | Sagel et al. | 424/401 |
| 6,576,712 B2 | 6/2003 | Feldstein et al. | 525/242 |
| 6,582,708 B1 | 6/2003 | Sagel et al. | 424/401 |
| 6,656,508 B2 | 12/2003 | Goldenberg et al. | 424/484 |
| 6,682,721 B2 | 1/2004 | Kim | 424/53 |
| 6,682,722 B2 | 1/2004 | Majeti et al. | 424/53 |
| 6,689,344 B2 | 2/2004 | Chang et al. | 424/53 |
| 6,719,995 B2 | 4/2004 | Rajaiah et al. | 424/435 |
| 6,790,460 B2 | 9/2004 | Shefer et al. | 414/489 |
| 6,884,426 B2 | 4/2005 | Sagel | 435/69.1 |
| 6,896,518 B2 | 5/2005 | Jacobs et al. | 433/215 |
| 6,905,672 B2 | 6/2005 | Rajaiah et al. | 424/49 |
| 6,916,463 B2 | 7/2005 | Lee et al. | 424/53 |
| 6,946,142 B2 | 9/2005 | Chang | 424/435 |
| 7,025,950 B2 | 4/2006 | Majeti | 424/49 |
| 7,067,115 B2 | 6/2006 | Orlowski et al. | 424/52 |
| 2001/0024657 A1 | 9/2001 | Lerner et al. | 424/448 |
| 2002/0006387 A1 | 1/2002 | Sagel et al. | 435/69.1 |
| 2002/0006388 A1 | 1/2002 | Sagel et al. | 424/401 |
| 2002/0012685 A1 | 1/2002 | Sagel et al. | 424/401 |
| 2002/0018754 A1 | 2/2002 | Sagel et al. | 424/49 |
| 2002/0146666 A1 | 10/2002 | Sagel et al. | 433/215 |
| 2003/0003421 A1 | 1/2003 | Bestenheider et al. | 433/215 |
| 2003/0059381 A1 | 3/2003 | Goodhart et al. | 424/53 |
| 2003/0152528 A1 | 8/2003 | Singh et al. | 424/53 |
| 2003/0170308 A1 | 9/2003 | Cleary et al. | 424/486 |
| 2003/0211056 A1 | 11/2003 | Sagel et al. | 424/401 |
| 2003/0219389 A1 | 11/2003 | Sagel et al. | 424/53 |
| 2004/0005277 A1 | 1/2004 | Willison et al. | 424/49 |
| 2004/0120903 A1* | 6/2004 | Sagel et al. | 424/53 |
| 2005/0260544 A1 | 11/2005 | Jones et al. | 433/217.1 |

FOREIGN PATENT DOCUMENTS

| | | | |
|---|---|---|---|
| CA | 2424055 | 4/2002 | A61K 9/00 |
| WO | WO 95/24872 A1 | 9/1995 | A61C 5/00 |
| WO | WO 01/01958 A1 | 1/2001 | A61K 9/00 |
| WO | WO 02/00182 | 1/2002 | A61K 7/20 |
| WO | WO 02/071968 A2 | 9/2002 | A61C 19/06 |
| WO | WO 03/015656 A2 | 2/2003 | A61C 19/06 |

OTHER PUBLICATIONS

Xantia™ Advertising Brochure, Manufactured by: Dexcel™ Pharma Technologies, Ltd. Jerusalem, Israel, Dist. By: Dexcel™ Pharma, Inc., Edison, NJ 08837 (date unknown).
Crest Whitestrips™ Advertising Brochure, Dist. By: Colgate-Palmolive Company, New York, NY 10022 (date unknown).
Office Action, dated Oct. 12, 2010, from U.S. Appl. No. 10/187,666.
Office Action, dated Oct. 15, 2009, from U.S. Appl. No. 10/187,666.
Office Action, dated Jan. 23, 2009, from U.S. Appl. No. 10/187,666.
Office Action, dated Aug. 6, 2008, from U.S. Appl. No. 10/187,666.
Office Action, dated Feb. 5, 2008, from U.S. Appl. No. 10/187,666.
Office Action, dated Sep. 20, 2007, from U.S. Appl. No. 10/187,666.
Office Action, dated Mar. 22, 2007, from U.S. Appl. No. 10/187,666.
Office Action, dated Jun. 28, 2006, from U.S. Appl. No. 10/187,666.
Office Action, dated Nov. 30, 2005, from U.S. Appl. No. 10/187,666.
Office Action, dated Oct. 1, 2004, from U.S. Appl. No. 10/187,666.
Office action mailed Jun. 21, 2012 for U.S. Appl. No. 10/985,709.

* cited by examiner

DEVICE AND METHOD FOR DELIVERING AN ORAL CARE AGENT

RELATED APPLICATIONS

This application is a continuation of U.S. application Ser. No. 10/985,709 entitled "Device and Method for Delivering an Oral Care Agent" filed Nov. 10, 2004, the entirety of which is hereby incorporated by reference.

FIELD OF THE INVENTION

This invention relates to the field of delivering an oral care agent, especially a tooth whitening agent, with a dental device.

BACKGROUND OF THE INVENTION

A variety of devices and methods have been developed to deliver a therapeutic or cosmetic agent to surfaces in the oral cavity. In particular, many systems which deliver a whitening agent to the teeth are available.

A person desiring whiter teeth can choose from professional whitening systems, or can purchase an over-the-counter tooth whitening device for use in the home. In the professional teeth bleaching market, dentists have traditionally used devices for delivery of home bleaching agents which are rigid and custom-fitted to an individual patient's dental arches. One type of delivery device is molded to closely fit a patient's dental arches. Another type of device is an "oversized" rigid custom dental appliance, which is formed by augmenting the facial surfaces of the teeth on stone models made from the patients' teeth, for example with linings such as die spacers or light-cured acrylics. A third type of device is a rigid, bilaminated custom-made dental appliance fabricated from materials ranging from soft porous foams to rigid, non-porous films. The non-porous, rigid thermoplastic shells of such bilaminated dental appliances may encase and support an internal layer of soft, porous foam which absorbs the bleaching agent.

After the custom appliance is fabricated, the dentist typically delivers the first bleaching treatment in the office, and instructs the patient on the proper procedure to dispense bleaching agent in the custom appliance at home. A sufficient amount of bleaching agent is provided so that the patient can perform the prescribed home bleaching regimen. The patient subsequently applies the bleaching agent daily (or as otherwise instructed) by dispensing the bleaching agent into the rigid custom dental appliance and placing the appliance over the dental arch for a specified period of time. At the end of a given treatment period, the dental appliance is removed, thoroughly cleaned to remove any remaining bleaching agent, and stored until the next application. The professional tooth whitening systems generally use a higher concentration of bleaching agent, and consequently the overall treatment period is shorter than that recommended for over-the-counter systems.

However, the rigid, custom-fabricated dental appliances used in professional tooth whitening systems require time-consuming and expensive office visits, laboratory tests and the fitting of each patient's dentition. Furthermore, any changes in the surface of the patient's teeth (such as fillings, crowns, and other accidental or therapeutic alterations of the dentition) affect the fit of the rigid custom dental appliance, and may warrant repeating the entire fabrication procedure. Refabrication of the appliance may also be required in the event of subsequent rebleaching treatments.

Moreover, patients who are inexperienced and unaware of the importance of precision often dispense an improper amount of bleaching agent into the appliance. Dispensing too little bleaching agent into the device results in a less efficacious treatment regimen. Dispensing an excessive amount of bleaching agent into the appliance can cause the agent to be displaced from the appliance into the oral cavity when the device is placed on the teeth, where the agent can be ingested. In addition to such displacement, the bleaching agent can spill or leak from these appliances into the oral cavity, causing, for example, an unpleasant taste sensation, gingival irritation, burning, edema, nausea or allergic reactions. The risk of the more serious side effects increases with the number of treatments, and becomes most significant after the multiple treatments typically required to attain acceptable clinical results. Patients who self-administer bleaching or other medicinal agents may also fail to provide the careful maintenance, cleaning, and storage necessary to ensure that the rigid custom dental appliance performs adequately throughout its entire service life.

There are additional drawbacks with custom bilaminated dental appliances, including occlusion and retention of bleaching agent. Furthermore, cleaning and maintenance of foam-lined dental appliances may be problematic, due to the high surface area and pore volume of the foam materials typically used in such appliances.

Oversized rigid custom dental appliances also have additional drawbacks, including occlusions in the augmented region, increased appliance fabrication time and cost, irritation from the lip of the appliance contacting the gingival region, and decreased retention of the bleaching agent within the target area.

In order to avoid the high cost and inconvenience of professional tooth whitening systems, one may purchase non-professional, "over-the-counter" tooth whitening systems. Some versions of the over-the-counter systems contain a generic "one size fits all" appliance and a container of bleaching gel to be dispensed into the appliance, for example as described in U.S. Pat. No. 3,416,527 of Greenberg and U.S. Pat. No. 3,527,219 of Hoef. However, such generic appliances often have a greater void between the interior walls of the appliance and the teeth as compared to most professionally fitted appliances. Hence, in order to insure intimate contact of the bleaching agent and the teeth surfaces, more bleaching agent is required. Furthermore, the poorer fit of the generic device means a greater loss of bleaching gel into the oral cavity, with the attendant problems described above for the professional tooth whitening appliances. Thus, the leakage problems of professional tooth whitening systems are exacerbated by over-the-counter systems in which the user dispenses the whitening agent into the device. The generic over-the-counter devices also tend to be bulky and uncomfortable in the mouth.

Over-the-counter systems with pre-dispensed bleaching agent are also available. The bleaching agents used in such over-the-counter systems are either viscous liquids or gels containing peroxide compounds. The peroxide compounds are typically provided in hydrated (i.e., active) form, or the peroxide compounds become hydrated due to moisture in the agent or the surrounding air. A typical bleaching agent is a carbamide peroxide gel, in which hydrogen peroxide is coupled to urea in either an anhydrous glycerin base or a soluble, aqueous carboxylic acid polymer base. Upon hydration, the carbamide peroxide breaks down into urea and active peroxide. The active peroxide subsequently breaks down into water and oxygen. Over time, the inherent instability of hydrated peroxide bleaching agents reduces the efficacy of tooth whitening systems with pre-dispensed bleaching agents. The shelf-life of such systems is therefore limited.

U.S. Pat. No. 5,310,563 of Curtis et al. discloses an over-the-counter tooth whitening device in which a putty-like material encapsulating the bleaching agent is molded around the teeth. The putty is held in place by mechanical engagement with undercut surfaces of the teeth, and by friction. The bleaching agent migrates from the composition to the gums and tooth surfaces, rather than being directly in contact with them, which significantly increases the required wearing time. The putty also tends to slip off the teeth, further reducing the efficacy of this type of system.

U.S. Pat. Nos. 5,575,654 and 5,863,202 of Fontenot disclose an over-the-counter tooth whitening system containing prepackaged moldable dental appliance that can be adapted to fit the dental arch, which contains a premeasured amount of medicinal or bleaching agent. It has been observed that the Fontenot device frequently has the problems of bulk and compromised fit. The pressure required to mold the device to the dental arch can also force the bleaching agent out of the device and into the oral cavity.

U.S. Pat. No. 5,980,249 of Fontenot describes a whitening system consisting of a prefabricated, U-shaped dental appliance of hydrophilic foam. The bleaching agent is incorporated or invested in the foam. This device has drawbacks similar to those described above for professional tooth whitening systems using custom bilaminated dental devices. Such drawbacks include occlusion and retention of bleaching agent in the foam, and extrusion of the bleaching agent into the oral cavity upon application of the pressure required to form the device to the user's teeth.

U.S. Pat. Nos. 5,879,691, 5,891,453 and 5,894,017 of Sagel et al. describe over-the-counter tooth whitening systems consisting of flat, flexible strips coated on one surface with an adhesive gel containing a bleaching agent. The strips are meant to be folded over the teeth by the user, with the bleaching agent in contact with, and holding the device onto, the teeth. However, the strip does not adhere well to the tooth surface, and the device tends to slip off the teeth in use.

The bleaching gel is also poorly attached to the Sagel et al. flexible strip, and often adheres to the user's fingers during the manipulations required to fold the strip in place over the dental arch. The potential for contamination of the strip by the user's fingers during routine manipulation is high. Moreover, the bleaching gel can be transferred from the user's fingers to the clothes (which may then be stained or bleached), or to sensitive areas of the body like the eyes, which may cause extreme discomfort. The bleaching gel will also adhere to itself and delaminate from the flexible strip if the user inadvertently folds the strip in upon itself during placement onto the teeth. Such delamination of the bleaching gel reduces the efficacy of the whitening system. Upon removal of the Sagel et al. strip from the teeth, a quantity of the bleaching agent can also adhere to the teeth. This leftover bleaching agent leaves an unpleasant taste in the mouth, and is easily ingested.

Moreover, most of the bleaching gel content of the Sagel et al. strip is delivered and begins to degrade as soon as the strip is placed in the mouth, resulting in reduced efficacy of the whitening system. Repeated and prolonged use of the Sagel et al. strips is thus required to achieve the desired whitening effect.

Over-the-counter whitening systems similar to those described in the Sagel et al. patents are disclosed in U.S. Pat. Nos. 5,989,569 and 6,045,811 of Dirksing et al. The Dirksing et al. system consists of a deformable flat wax strip carrying the same type of bleaching gel as the Sagel et al. strips. Here again, the bleaching gel is poorly adhered to the wax strips, and the Dirksing et al. system likely suffers from the same problems of difficulty of use and reduced efficacy as described above for the Sagel et al. strips.

U.S. Pat. App. 2004/0005277 of Willison et al. describes over-the-counter tooth whitening systems comprising a permanently deformable backing layer, a foam anchor layer and an oral care layer comprising a medicament such as a bleaching agent. This device overcomes some of the problems associated with the above-described known inventions. The device is less bulky than the pre-formed over the counter devices, but still has a substantial bulk due to the thickness of the foam anchor layer. The bulk causes potential comfort and conformability problems. The bulk also adds to the expense of the die cutting operations used in making the devices. In addition, the foam anchor layer readily absorbs water, thereby diluting the oral care active, which in turn may reduce the efficacy of the device. The layered structure of the device increases the possibility of delamination during use or removal. For example, when a user removes the device, the oral care layer may continue to adhere to the surface of the teeth, separating from the wax backing layer and/or the foam anchor layer.

Many of the known professional and over-the-counter tooth whitening systems can also be used to deliver other oral care agents, such as medicines or antibiotics, to the teeth and gingival tissue. However, the drawbacks described above for the tooth whitening systems are also present when the systems are used to deliver other oral care agents.

What is needed, therefore, is an over-the-counter device for delivering an oral care agent, for example a tooth whitening agent, in which a pre-measured amount of oral care agent is contained within a device that is firmly held onto a user's teeth, which does not release the oral care agent into the oral cavity in appreciable quantities, which is relatively non-bulky in structure, and which does not delaminate during use or removal. The device should also be configured so that the user does not contact the oral care agent during routine manipulation of the device into place over the dental arch. The layer which delivers the oral care agent should also be sufficiently secured to the device so that little or no residue is left on the user's fingers if the layer is inadvertently touched, and no residue is left on the teeth upon removal of the device. Furthermore, the oral care agent should be activated and released from the device over time, so that efficacy of the agent is maximized and not diluted, and the number and duration of each application is reduced.

SUMMARY OF THE INVENTION

It has been found that the deficiencies of both the professional and over-the-counter oral care agent delivery systems discussed above are overcome by the oral care agent delivery devices of the invention.

The device of the invention comprises a permanently deformable backing layer, a non-woven binding material comprising a first part and a second part, and an oral care layer. The device is sized to fit over a plurality of teeth in an upper or lower dental arch of a subject. The oral care layer comprises at least one oral care agent and at least one hydrophilic polymer. The binding material is a non-woven material that binds the oral care layer and the backing layer. The first part of the binding material is substantially invested in at least a portion of the oral care layer, and the second part of the binding material is substantially invested in at least a portion of the backing layer. The oral care layer has an adhesiveness when hydrated relative to the surface of the teeth of wearer that is sufficient to retain the device on the user's teeth when placed thereon.

The invention also provides a device that has a substantially non-flat cross section.

The invention also provides a device in which the oral care agent is activated on hydration of the oral care layer.

The invention also provides a device comprising a sustained release oral care layer.

The invention also provides a method for delivering an oral care agent to a plurality of teeth in an upper or lower dental arch in a subject, comprising providing a device which comprises a permanently deformable backing layer, a non-woven binding material with a first part and a second part, and an oral care layer. The device is sized to fit over a plurality of teeth in an upper or lower dental arch of a subject. The oral care layer comprises at least one oral care agent and at least one hydrophilic polymer. The first part of the binding material is substantially invested in at least a portion of the oral care layer, and the second part of the binding material is substantially invested in at least a portion of the backing layer. The oral care layer has an adhesiveness when hydrated relative to the surface of the teeth of a wearer that is sufficient to retain the device on the wearer's teeth when placed thereon. The oral care agent is delivered by wetting the teeth or the oral care layer, placing the device over the teeth of a dental arch, and pressing the device to the teeth by manual pressure so that the oral care layer is in contact with at least the front surface of the teeth. The device is then left on the teeth for a sufficient time to achieve the desired result, whereupon it is removed from the teeth and discarded. The process of delivering the oral care agent can be repeated as necessary.

The invention further provides a method for delivering a tooth whitening agent to a plurality of teeth in an upper or lower dental arch in a subject, comprising providing a device comprising a permanently deformable backing layer, a non-woven binding material with a first part and a second part, and an oral care layer. The device is sized to fit over a plurality of teeth in an upper or lower dental arch of a subject. The oral care layer comprises at least one oral care agent and at least one hydrophilic polymer. The first part of the binding material is substantially invested in at least a portion of the oral care layer, and the second part of the binding material is substantially invested in at least a portion of the backing layer. The oral care layer has an adhesiveness when hydrated relative to the surface of the teeth of a wearer that is sufficient to retain the device on the wearer's teeth when placed thereon. The tooth whitening agent is delivered by wetting the teeth or the device, pressing the device over the teeth, and pressing the device to the teeth by manual pressure so that the oral care layer is in contact with at least the front surface of the teeth. The device is then left on the teeth for a sufficient time to achieve the desired result whereupon it is removed from the teeth and discarded. The process of delivering the tooth whitening agent can be repeated as necessary.

The invention further provides a method of making a device for delivering an oral care agent, which device comprises a permanently deformable backing layer, a non-woven binding material with a first part and a second part, and an oral care layer. The method comprises the steps of providing the permanently deformable backing layer, pressing the binding material into the backing layer such that the second part of the binding material substantially invests in at least a portion of the backing layer, and extruding the oral care layer onto the binding material such that the first part of the binding material substantially invests in at least a portion of the oral care layer.

DETAILED DESCRIPTION OF THE INVENTION

Figure 1:
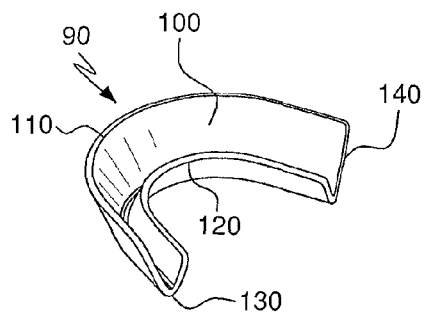
FIG. 1 is an isometric view of one embodiment of a device of the invention as seen from the back.

The invention concerns devices which deliver an oral care agent to the surface of the teeth. The present devices are particularly well-suited to delivering a tooth whitening agent to the surface of the teeth.

The construction of the device, and the characteristics of the various layers which comprise the device, serve to overcome the disadvantages of prior commercial or over-the-counter delivery systems discussed above. For example, the present device contains a pre-measured amount of oral care agent in an oral care layer, so there is no danger of over- or under-filling by the user. Because the oral care agent is not dispensed into the device by the user, the chance of contamination of the oral care layer by improper or careless filling of the device is eliminated. Moreover, the physical characteristics of the oral care layer are such that oral care agent does not spill or squeeze out into the oral cavity in appreciable quantities when the device is placed on the teeth.

The present device can be configured so that the user does not contact the oral care agent during routine manipulation of the device into place over the dental arch, but rather contacts only the backing layer. In any event, the oral care layer is sufficiently secured to the device by a non-woven binding material so that no residue is left on the user's fingers if the oral care layer is inadvertently touched. Moreover, no or minimal residue of the oral care layer is left on the teeth upon removal of the device. In some embodiments, as discussed in more detail below, the oral care agent is activated and/or released from the oral care layer over time, so that efficacy of the agent is maximized and the number and duration of each application is reduced.

All percentages given herein are by weight.

The device of the invention comprises two layers: a permanently deformable backing layer and an oral care layer. The two layers preferably are in contact with one another and preferable form an adhesive bond at the contact point. The two layers are further held together by a non-woven binding material. As used herein a non-woven binding material is a non-woven material that binds two or more chemicals, or two or more layers together through physical, mechanical or chemical means. The binding material of the invention comprises a first part and a second part. The first part of the binding material is substantially invested in the oral care layer and the second part of the binding material is substantially invested in the backing layer. The binding material preferably does not create a separate layer. Rather, at least a portion of the binding material is invested in the oral care layer and at least a portion of the binding material is invested in the backing layer, and there is no portion of the binding material that is not invested in either the oral care layer or the backing layer. The intended result is a device with two layers, the oral care layer and the backing layer, in contact with one another and forming an adhesive bond there between with the binding material aiding in the adhesive stability of the bond.

The backing layer comprises a thin, flexible layer of permanently deformable material. As used herein "permanently deformable" means that the backing layer retains any shape into which it is formed by application of slight pressure e.g., less than about 250,000 Pascals per square centimeter. Thus, the device readily conforms to the surface of the teeth and adjoining soft tissue across the dental arch in the user's mouth without tearing, cracking or breaking. The material which comprises the backing layer preferably has visco-elastic properties which allow the backing layer to creep as well as bend when pressure is applied to the device.

For example, a user can form the device around the teeth of the upper or lower dental arch by applying normal manual pressure to the backing layer with the tips of the fingers and thumbs. Assuming the surface area of the average adult finger or thumb tip is approximately one square centimeter, the normal pressure generated by the finger and thumb tips is about 100,000 to about 150,000 Pascals (i.e., about 3 lbs. or 1.36 kg) per square centimeter. The pressure is typically applied to the device by each finger and thumb tip for about one or two seconds. Once the pressure applied to the backing layer by the tips of the fingers and thumbs is removed, the device retains the shape of the dental arch and surface of the teeth and adjoining soft tissue onto which it was formed.

As used herein, "adjoining soft tissue" means the tissue surrounding the tooth structure, including the marginal gingiva, gingival sulculus, inter-dental gingiva, and the gingival gum structure on the lingual and buccal surfaces up to and including the muco-gingival junction and the pallet.

The backing layer can be any thickness that allows it to retain its permanently deformable characteristics; i.e., the layer cannot be so thin as to fail to retain its shape after application of pressure, and the layer cannot be so thick as to resist deformation. Preferably, the backing layer is from about 0.025 mm (1 mil) to about 0.508 mm (20 mils) thick, more preferably about 0.125 mm (5 mil) to about 0.457 mm (18 mil) thick, and particularly preferably about 0.38 mm (15 mil) thick.

The backing layer preferably comprises a non-polymeric material such as a wax (e.g., microcrystalline or paraffin waxes), a tackifier (e.g., a natural or synthetic resin, such as a hydrocarbon resin), or mixtures thereof that have the properties discussed above.

Paraffin waxes are low-molecular weight waxes composed of straight-chain hydrocarbons, with melting points ranging from 48° C. to 75° C. These waxes are typically highly refined and have a low oil content. The paraffin waxes can be obtained by the distillation of crude oil, or can be produced synthetically, for example by Fischer-Tropsch synthesis. Paraffins produced by Fischer-Tropsch synthesis contain straight chain hydrocarbon molecules comprising methylene groups, which may have either even or odd numbers of carbons. The synthetic paraffins typically have a molecular weight range from about 300 g/mol to about 1400 g/mol, and melting points of about 48° C. to 75° C.

Microcrystalline waxes are flexible and amorphous-like in appearance, and have a higher tensile strength and smaller crystals than the paraffin waxes. The molecular weight of the commercially available microcrystalline waxes is generally from about 580-700 g/mol, with the average molecule containing 41-50 carbon atoms. Straight-chain molecules may be present in the microcrystalline waxes, but the largest proportion of molecules are branched-chain hydrocarbons and some ring-type compounds. The melting point of microcrystalline waxes is typically higher than the paraffin waxes; e.g., from about 60° C. to about 95° C.

Preferred microcrystalline and paraffin waxes for use in the present invention, and their physical characteristics, are given below in Table 1. A particularly preferred wax is Microcrystalline 180/185 (#146), available from Koster-Keunen, Inc., Watertown, Conn., 06795. Other suitable waxes include #165 sheet wax, available from Freeman Mfg. & Supply Co., Avon, Ohio, 44011-1011.

TABLE 1

| Wax | Congealing Point (ASTM D938) | Melting Point | Acid Value (USP 401) | Saponification Value (USP 401) | Penetration (ASTM D1321) | Viscosity (ASTM D2161) | Oil Content (wt %; ASTM D721) | Color (Visual) |
| --- | --- | --- | --- | --- | --- | --- | --- | --- |
| Microcrystalline 180/185 (#146)[1] | 77-81° C. | 77-85° C. | <1 | <1 | 10-16, 100 g, 5 s, @25° C. | 70-84@ 99° C. | 1.5% max | white to light yellow |
| Microcrystalline 193/198 (#118P)[1] | 80-92° C. | 89-92° C. | <1 | <1 | 5-9, 100 g, 5 s, @25° C. | — | — | light yellow |
| Paraffin 140/145 (#126G)[1] | 82-92° C. | 60-63° C. | 0.1 max | 0.1 max | 11-18, 100 g, 5 s, @25° C. | — | 1.5% | — |
| Microcrystalline Wax S.P. 16[2] | — | 82-88° C. | Nil | Nil | 13-19, 100 g, 5 s, | 75-90@ 99° C. | — | yellow |

TABLE 1-continued

| Wax | Congealing Point (ASTM D938) | Melting Point | Acid Value (USP 401) | Saponification Value (USP 401) | Penetration (ASTM D1321) | Viscosity (ASTM D2161) @25° C. | Oil Content (wt %; ASTM D721) | Color (Visual) |
|---|---|---|---|---|---|---|---|---|
| synthetic paraffin[1] (CAS 8002-74-2) | 78-105° C. | — | — | — | — | — | not greater than 0.75% | white |

[1]Available from Koster-Keunen, Inc., Watertown, CT, 06795.
[2]Available from Strahl & Pitsch, Inc., West Babylon, NY, 11704.

The backing layer can also comprise hydrocarbon resins. Hydrocarbon resins are amorphous, glassy, typically low molecular weight hydrocarbons with defined molecular weight ranges. Hydrocarbon resins suitable for producing the backing layer include the "Escorez" 5300 series of water-white, clear cycloaliphatic hydrocarbon resins (CAS #68132-00-3) available from ExxonMobil Chemical, Houston, Tex. 77079-1398. A preferred hydrocarbon resin is Escorez 5380. The typical physical characteristics of the Escorez 5300 series hydrocarbon resins are given in Table 2 below.

TABLE 2

| Resin | 5380 | 5300 | 5320 | 5340 | ExxonMobil Test Method[2] |
|---|---|---|---|---|---|
| Softening Point, R&B, ° C. | 85 | 105 | 122 | 140 | ETM 22-24 |
| Color | | | | | |
| Ylt, initial[1] | 1 | 1 | 1 | 1 | ETM 22-13 |
| Yl, Aged 5 hours at 175° C.[1] | 3 | 3 | 3 | 3 | ETM 22-14 |
| Molten Gardner Color | 1 | 1 | 1 | 1 | ETM 22-12 |
| Melt Viscosity (Brookfield) | | | | | ETM 22-31 |
| Test Temperature, ° C. | 140 | 140 | 160 | 180 | |
| Cps | 700 | 4,500 | 5,000 | 4,500 | |
| Molecular Weight | | | | | ETM 300-83 |
| $\overline{M}w$ | 370 | 420 | 430 | 460 | |
| $\overline{M}n$ | 160 | 210 | 190 | 230 | |
| $\overline{M}z$ | 900 | 900 | 950 | 1000 | |
| Tg, ° C. | 35 | 55 | 65 | 85 | ETM 300-90 |
| Specific Gravity, 20/20° C. (IPOH) | 1.1 | 1.1 | 1.1 | 1.1 | ETM 22-28 |
| Ash Content, wt. % | <0.1 | <0.1 | <0.1 | <0.1 | ETM 22-05 |
| Acid Number, mg KOH/g | <1 | <1 | <1 | <1 | ETM 22-49 |
| Volatility, wt % | 10.0 | 4.0 | 1.5 | 0.5 | ETM 22-32 |

[1]Solution color as determined by measurement of a 50% (by weight) product in toluene mixture.
[2]The entire disclosures of the ExxonMobil Test Methods are herein incorporated by reference.

The backing layer can optionally be colored, so that the device is visibly obtrusive when worn. For example, the backing layer (and thus the device itself) can be colored with bright or vibrant colors which a consumer may find pleasing. The backing layer can therefore comprise a colorizing compound, such as, for example, a dye, pigment or substance that can impart color when added to the material forming the backing layer.

For example, colorizing compounds of the type commonly used with foods, drugs, or cosmetics in connection with the human body, especially color additives permitted for use in foods which are classified as "certifiable" or "exempt from certification," can be used to color the backing layer. The colorizing compounds used to color the backing layer can be derived from natural sources such as vegetables, minerals or animals, or can be man-made counterparts of natural derivatives.

Colorizing compounds presently certified under the Food Drug & Cosmetic Act for use in food and ingested drugs include dyes such as FD&C Red No. 3 (sodium salt of tetraiodofluorescein); Food Red 17 (disodium salt of 6-hydroxy-5-{(2-methoxy-5-methyl-4-sulphophenyl)azo}-2-naphthalenesulfon-ic acid); Food Yellow 13 (sodium salt of a mixture of the mono and disulfonic acids of quinophthalone or 2-(2-quinolyl)indanedione); FD&C Yellow No. 5 (sodium salt of 4-p-sulfophenylazo-1-p-sulfophenyl-5-hydroxypyrazole-3 carboxylic acid); FD&C Yellow No. 6 (sodium salt of p-sulfophenylazo-B-napthol-6-monosulfonate); FD&C Green No. 3 (disodium salt of 4-{[4-(N-ethyl-p-sulfobenzylamino)-phenyl]-(4-hydroxy-2-sulfonium-phenyl)-methylene}-[1-(N-ethyl-N-p-sulfobenzyl)-3,5-cyclohexadienimine]); FD&C Blue No. 1 (disodium salt of dibenzyldiethyl-diaminotriphenylcarbinol trisulfonic acid anhydrite); FD&C Blue No. 2 (sodium salt of disulfonic acid of indigotin); FD&C Red No. 40; Orange B; and Citrus Red No. 2; and combinations thereof in various proportions.

Colorizing compounds exempt from FDA certification include annatto extract; beta-apo-8'-carotenal; beta-carotene; beet powder; canthaxanthin; caramel color; carrot oil; cochineal extract (carmine); toasted, partially defatted, cooked cottonseed flour; ferrous gluconate; fruit juice; grape color extract; grape skin extract (enocianina); paprika; paprika oleoresin; riboflavin; saffron; turmeric; turmeric oleoresin; vegetable juice; and combinations thereof in various proportions.

The form of the colorizing compound for use in the present invention preferably includes dye form additives, but may also include lake forms which are compatible with the material comprising the backing layer. Water soluble dyes, provided in the form of powders, granules, liquids or other special-purpose forms, can be used in accordance with the present method. Preferably, the "lake", or water insoluble form of the dye, is used for coloring the backing layer. Lake form additives are preferred over straight dyes because of their greater stability and lesser tendency to color bleed. For example, if a suspension of a colorizing compound is to be used, a lake form additive can be employed. Suitable water insoluble dye lakes prepared by extending calcium or aluminum salts of FD&C dyes on alumina include FD&C Green #1 lake, FD&C Blue #2 lake, FD&C RED #30 lake and FD&C # Yellow 15 lake.

Other suitable colorizing compounds include non-toxic, water insoluble inorganic pigments such as titanium dioxide; chromium oxide greens; ultramarine blues and pinks; and ferric oxides. Such pigments preferably have a particle size in the range of about 5 to about 1000 microns, more preferably about 250 to about 500 microns.

The concentration of the colorizing compound in the backing layer is preferably from about 0.05% to about 10%, and is more preferably from about 0.1% to about 5%.

More than one colorizing compound can be present in the backing layer, so that multiple colors are imparted to the backing layer. The multiple colors in the backing layer can be patterned into stripes, dots, swirls or any other design which a consumer may find pleasing. The colorizing compound can also be used with other appearance-enhancing substances such as glitter particles.

The backing layer can also be embedded or decorated with decorative items such as beads, rhinestones, or the like, as long as these items do not interfere with the properties of the backing layer required for proper deformation of the device onto the teeth, as described above. The backing layer can also display letters, words, or images designed to be pleasing or attractive to a consumer.

The backing layer can also comprise additional ingredients including coloring compounds as described above; food additives; flavorants; sweeteners; and preservatives.

Any natural or synthetic flavorant or food additive, such as those described in Chemicals Used in Food Processing, Pub. No. 1274, National Academy of Sciences, pages 63-258 (the entire disclosure of which is herein incorporated by reference) can be used. Suitable flavorants include wintergreen, peppermint, spearmint, menthol, fruit flavors, vanilla, cinnamon, spices, flavor oils and oleoresins, as known in the art. The amount of flavorant employed is normally a matter of preference, subject to such factors as flavor type, individual flavor, and strength desired. Preferably, the backing layer comprises from about 0.1% to about 5% flavorant.

Sweeteners useful in the present invention include sucrose, fructose, aspartame, xylitol and saccharine. The choice of sweeteners and the desired "sweetness" dictates the amount of sweetener to be added to the backing layer. Preferably, the backing layer comprises sweeteners in an amount from about 0.001% to about 5.0%.

The non-woven binding material preferably comprises a spun bonded polypropylene. The material and structure of the first part and the second part are preferably the same. The primary basis for the distinction between the first part and the second part is the layer into which the individual layer is invested. The first part of the binding material is substantially invested in the oral care layer. The second part of the binding material is substantially invested in the backing layer. Preferably, the first part of the binding material comprises about one half of the binding material and the second part of the binding material comprises about one half of the binding material. Thus, about one half of the binding material is invested in the oral care layer and about one half of the binding material is invested in the backing layer.

Preferably, the face of the backing layer contacting the binding material is softened by heating prior to being invested by the binding material.

In one embodiment, the second part of the binding material is co-extensive with the backing layer. As used herein, "coextensive" means having substantially the same length and width as the backing layer. In other embodiments, the binding material is of smaller dimensions (i.e., in length and/or width) than the backing layer, so that the material comprising the backing layer extends beyond one or more edges of the binding material when the binding material is invested in the backing layer.

The binding material preferably has minimal flexural stiffness; that is, the binding material does not resist deformation when the device is pressed into place on the teeth of the user. Thus, the binding material can be any thickness which does not interfere with the permanent deformation of the device when pressure is applied by the user. Preferably, the binding material is from about 0.089 mm (3.5 mils) to about 0.279 mm (11 mils) thick, more preferably about 0.114 mm (4.5 mils) to about 0.203 mm (8 mils) thick, and particularly preferable at about 0.152 mm (6 mils) thick. Proper binding material thickness is essential in ensuring that the oral care layer does not shrink away from the binding layer, resulting in the oral care layer delaminating from the backing layer.

The binding material can be any non-woven material. Non-woven materials are a category of materials made primarily of textile fibers that are not processed on conventional spindles, looms, or knitting machines, but rather the fibers are held together by bonding, fusing, or other chemical, thermal or mechanical means. For example, structurally, the non-woven material can be a felt, or chemically, it can be from the group consisting of a polyolefin (e.g. polyethylene and polypropylene), polyester, polyurethane, polyamide, polyaramide and glass. Preferably, the binding material comprises a spun bonded non-woven (i.e., a non-woven fabric formed by filaments that have been extruded, drawn, then laid on a continuous belt). More preferably, the binding material comprises a spun bonded polypropylene, for example Typar® or Remay®. However, the binding material can also be spunlaced (non-woven fabric produced by entangling of fibers in a repeating pattern to form a strong fabric that is free of binders), carded (non-woven fabric produced by a process similar to carding wool in textile industry), "hook" or "loop" fabrics used in hook and loop fasteners, or other known variations.

The binding material can also comprise a color or pigment, which imparts a color or hue to the binding material. In embodiments where the backing layer is uncolored but the binding material is colored, the color of the binding material is preferably visible, thus making the device obtrusive when worn. The binding material can comprise the same colorizing compounds in the same preferred concentrations listed above for coloring the backing layer.

The oral care layer comprises at least one oral care agent and at least one hydrophilic polymer. A portion of the oral care layer is substantially invested by a first part of the non-woven binding material. The oral care layer is generally co-extensive with the binding material.

The oral care layer has minimal flexural stiffness; that is, the oral care layer does not resist deformation when the device is pressed into place on the teeth of the user. Thus, the oral care layer can be any thickness which does not interfere with the permanent deformation of the device when pressure is applied by the user, and which allows a suitable amount of oral care agent to be contained within the layer for delivery to the teeth. Preferably, the oral care layer is from about 0.025 mm to about 4 mm thick, more preferably about from about 0.125 mm to about 1.5 mm thick, particularly preferably from about 0.25 mm to 1.0 mm, for example, about 0.3 mm thick.

A portion of the oral care layer is invested by the first part of the binding material, meaning that more than an appreciable amount of the oral care layer penetrates below the surface of the first part of the binding material to form a oral care layer/binding material composition. The portion of the oral care layer that is not invested by the binding material is located immediately adjacent to the oral care layer/binding material composition.

The oral care layer has an adhesiveness when hydrated that is sufficient to adhere the surface of the teeth and surrounding soft tissue when the device is conformed to the teeth and dental arch. The oral care layer should adhere to the teeth and surrounding soft tissue for as long a period of time as necessary for the oral care agent to be delivered and effect the desired result. Typically, the device is left on the teeth for approximately 15 minutes to one hour, although shorter or longer times are contemplated. Methods for delivering an oral care agent to the teeth with the present device are described in more detail below.

The oral care layer also has sufficient adhesiveness and cohesiveness to the teeth so that the device is resistant to inadvertent removal and yet is easily removed from the teeth. The substantial investment of the binding material in the oral care layer causes a bond between the binding material and the oral care layer that is greater than the strength of the adhesive bond between the oral care layer and the teeth. Moreover, the substantial investment of the binding material in both the oral care layer and the backing layer prevents the device from delaminating upon removal from the teeth.

The adhesive properties of the oral care layer should not be weakened or destroyed by exposure to moisture or high humidity. In one embodiment, the adhesive properties of the oral care layer with respect to bonding to the teeth are enhanced by hydration, for example with water or saliva.

As used herein, "adhesion" or "adhesiveness" refers to the molecular attraction exerted between surfaces of bodies in contact. As used herein, "cohesion" or "cohesiveness" refers to the molecular attraction by which the particles of a body are united throughout the mass.

Adhesiveness can be expressed in units of force per distance (e.g., "Newtons/meter" or "N/m"), and cohesiveness can be expressed in terms of tack. A suitable strength for an adhesive bond between the oral care layer and the surface of the teeth ranges from about 200 to about 400 N/m. A suitable tack for the oral care layer is greater than about 50 g/cm².

Adhesiveness and tack can be measured by standard tests such as 90 or 180 degree peel force tests, rolling ball-style tests, tack tests (e.g., the PKI or TRBT tack determination methods), and static shear tests, and other tests such as are known in the art.

For example, a modified commercially available surface tensiometer suitable for measuring the adhesive strength of bioadhesives is described in U.S. Pat. No. 4,615,697 of Robinson, the entire disclosure of which is herein incorporated by reference. The adhesiveness and tack of the present oral care layer can also be determined using a TA.XT2 Texture Analyzer (Texture Technologies Corp.) together with an XT.RA Dimension software package (Stable Micro Systems, Ltd.), according to the manufacturer's instructions.

According to the operation of a TA.XT2 texture analyzer, the device for testing is mounted on a block with the oral care layer exposed, and a probe attached to the TA.XT2 texture analyzer is moved at a fixed speed against the adhesive surface of the oral care layer, distorting the oral care layer to a fixed penetration depth. The probe is permitted to dwell at the penetration depth for a fixed time. The probe is then withdrawn from the oral care layer at a fixed speed, and the peak force required to detach the probe from the oral care layer surface is measured. Suitable conditions for measuring the adhesiveness and tack of the present oral care layer with the TA.XT2 Texture Analyzer are a probe diameter of 0.80 cm, a penetration depth of 0.1 mm, a penetration rate of 1.0 mm/sec, a dwell time of 10 sec, and a withdrawal rate of 5.0 mm/sec.

In some embodiments, the oral care agent is entrapped within the oral care layer by a matrix formed by the hydrophilic polymer. The oral care agent is released from the hydrophilic polymer matrix upon hydration and swelling of the hydrophilic polymer, whereupon the agent is delivered to the teeth to produce the desired effect.

Preferably, prior to release and/or activation with water or saliva, the oral care agent within the oral care layer is stable such that minimal potency is lost during normal storage conditions (i.e., in a vacuum sealed package at ambient temperature and humidity) for greater than one year prior to use.

Preferably, the oral care layer comprises a pressure-sensitive adhesive comprising an oral care agent and a hydrophilic polymer that is made tacky (i.e., it is rendered pressure-sensitive) at room temperature by addition of a water-soluble plasticizer that is miscible with the polymer.

Hydrophilic polymers useful in the oral care layer are characterized as being solid at room temperature; that is, as having a glass transition temperature $T(g)$, or melting point $T(m)$, higher than about 25° C. and lower than about 120° C., and more preferably higher than about 30° C., and lower than about 100° C. The hydrophilic polymers also preferably have a hydrophilicity as measured by water uptake greater than about 25%. Suitable polymers include polysaccharides (e.g., starches and starch derivatives, cellulose-derivatives such as sodium carboxymethyl cellulose or "Na-CMC"), and water-soluble synthetic polymers (e.g., 2-acrylamido-2-methyl-propanesulfonic acid or "poly AMPS", polyvinyl pyrrolidone or "PVP," polyvinyl alcohol or "PVA," hydroxypropyl cellulose or "HPC", polyethylene oxide or "PEO", polyacrylic acid or "PAA," and carboxylic acid polymers such as the Carbopols and Carbomers available from B. F. Goodrich); polypeptides; and natural gums such as xanthan gum, karaya gum, and gelatin.

Plasticizers useful in the oral care layer are characterized as being liquid at room temperature and having a boiling point higher than about 80° C. Suitable plasticizers include glycerin, sorbitol, any of the glycols, polysorbate 80, triethyl titrate, acetyl triethyl titrate, and tributyl titrate.

Preferably, the hydrophilic polymer comprising the oral care layer comprises crosslinked or non-crosslinked polymers such as 2-acrylamido-2-methyl-propanesulfonic acid (poly AMPS); polyvinyl pyrrolidone (PVP); polyethylene oxide (PEO); polyacrylates (e.g., the Eudragits™, available from Rohm America, Inc., Piscataway, N.J.); polyvinyl alcohol (PVA); carboxylic acid polymers (e.g., Carbopols™ and Carbomers™ available from B. F. Goodrich). The Eudragits™ are characterized as one of (1) an anionic copolymer based on methacrylic acid and methylmethacrylate wherein the ratio of free carboxyl groups to the ester groups is approximately 1:1, (2) an anionic copolymer based on methacrylic acid and methylmethacrylate wherein the ratio of free carboxyl groups to the ester groups is approximately 1:2, (3) a copolymer based on acrylic and methacrylic acid esters with a low content of quaternary ammonium groups wherein the molar ratio of the ammonium groups to the remaining neutral methacrylic acid esters is 1:20, or (4) a copolymer based on acrylic and methacrylic acid esters with a low content of quaternary ammonium groups wherein the molar ratio of the ammonium groups to the remaining neutral methacrylic acid esters is 1:40.

Particularly preferred are oral care layers comprising the poly(AMPS)-based pressure sensitive adhesives described in U.S. Pat. No. 4,581,821 of Cahalan et al., or comprising the PEG-PVP-based pressure sensitive adhesives described in U.S. Pat. No. 6,576,712 of Feldstein et al, the entire disclosures of which are herein incorporated by reference.

The oral care layer can also comprise a scrim, which serves to further reinforce the oral care layer against fragmentation and delamination. Preferably, the scrim is embedded in the portion of the oral care layer that is not occupied by the first part of the binding material. The scrim can comprise a variety of woven or non-woven materials or perforated sheetlike materials which are known in the art. Suitable woven materials for forming the scrim include cloth or gauze formed of natural or synthetic fibers such as cotton; polyester (e.g., DACRON® fibers, and SONTARA® fabrics such as polyester grades 8000, 8027 and 8100, E. I. dupont de Nemours & Co.); polyolefins (e.g., polyethylene, polypropylene and the like); polyurethane; polyamide (e.g., NYLON® fiber); polyaramide (e.g., KEVLAR® fiber); and glass (e.g., FIBERGLAS™ fiber). The woven materials for forming the scrim can be a conventional weave or a nonconventional weave such as either of the "hook" or "loop" fabrics used in hook and loop fasteners.

Suitable non-woven materials for forming the scrim include felt and synthetic fibers such as polyester; polyolefins (e.g., polyethylene, polypropylene and the like); polyurethane; polyamide (e.g., NYLON® fiber); polyaramide (e.g., KEVLAR® fiber); and glass (e.g., FIBERGLAS™ fiber). Particularly preferred is a non-woven polyolefin fabric, such as DELNET® fabric from DelStar Technologies, Inc. (Middletown, Del.).

Suitable perforated sheetlike materials for forming the scrim include fine pitch polypropylene net.

Preferably, the scrim should be free of objectionable taste or odor, and be safe for use in the mouth. The material forming the scrim also preferably has a melting temperature above the melting or softening temperature of the material forming the oral care layer.

In an embodiment, the scrim is embedded in the oral care layer. The scrim can be embedded in the oral care layer by techniques well-known in the art. For example, the scrim can be sandwiched between layers comprised of the materials that make up the oral care layer. The oral care layer can also be extruded directly onto the scrim, whereupon the melted material comprising the oral care layer flows through and around the openings in the scrim material. Upon cooling of the melted oral care layer material, the scrim is entirely surrounded by the oral care layer. Other methods for embedding a non-woven, woven or perforated sheet scrim in the oral care layer will be apparent to those of ordinary skill in the art.

In one embodiment, the material comprising the oral care layer releases the oral care agent over time, so that activated oral care agent is delivered to the teeth throughout the entire period during which the device is used. Such oral care layers are called "sustained-release" oral care layers. In one embodiment, oral care agent is delivered to the teeth in a substantially uniform quantity per unit time by the sustained-release oral care layer. In another embodiment, an oral care agent is delivered in non-uniform quantities per unit time. For example, larger quantities of activated oral care agent can be delivered in a given portion of the treatment period as compared to the other portions; e.g., more oral care agent can be delivered during the first quarter, third or half of the treatment period than in the remaining portions of the treatment period.

The sustained-release oral care layer delivers the oral care agent by diffusion of the oral care agent through the oral care layer toward the surface of the teeth and surrounding tissue. Diffusion outward into the oral cavity is blocked by the backing layer, which is substantially impermeable to the oral care agent and to saliva under the conditions in which the device is used. A limited amount of oral care agent may escape into the oral cavity by diffusion outward from the edges of the device during use; however, this should have a negligible impact on the safety and efficacy of the device. It is preferred that the oral care layer is not substantially degradable or erodible, so that little to no degradation by-products are produced and released into the oral cavity during use of the device.

The rate of delivery of the oral care agent from the oral care layer to the teeth can be controlled by adjusting the concentration of hydrophilic polymer and plasticizer in the oral care layer. Generally, a higher concentration of hydrophilic polymer in the oral care layer results in a higher cohesive strength of the layer, which in turn lowers the rate of release of the oral care agent. The cohesiveness of hydrophilic polymer-based materials suitable for use in the oral care layer can be adjusted to a desired value according to principles well-known in the art; see, for example, U.S. Pat. No. 4,581,821 of Cahalan et al., supra, and U.S. Pat. No. 6,576,712 of Feldstein et al., supra.

The concentration of oral care agent in the oral care layer required to deliver the desired amount of oral care agent to the teeth and surrounding tissue can vary depending on factors such as the type, length and frequency of treatment to be performed, the severity of the condition, the age and health of the user, and the like. One of ordinary skill in the art can readily vary the concentration of the oral care agent in the oral care layer in order to achieve a desired result. Generally, the amount of oral care agent in the oral care layer is preferably from about 0.01% to about 40%, more preferably from about 0.1% to about 20%, most preferably from about 0.5% to about 14%, and particularly preferably from about 1% to about 10%. Preferred amounts of a given oral care agent to be included in the oral care layer are provided below.

The oral care agent can be any pharmaceutically active agent useful in treating physiological conditions involving the teeth and surrounding tissue. As used herein, a "pharmaceutically active agent" is any substance that can be released from the oral care layer to treat an undesirable physiological condition. Undesirable, physiological conditions involving the teeth or surrounding tissue which are amenable to treatment with the present device include: halitosis; periodontal and oral infections; periodontal lesions; dental caries or decay; gingivitis; and other periodontal diseases.

The pharmaceutically active oral care agent can be, for example, non-steroidal anti-inflammatories/analgesics (preferably 0.1-5% in the oral care layer); steroidal anti-inflammatory agents (preferably 0.002-0.5% in the oral care layer); local anesthetics (preferably 0.05-2% in the oral care layer); bactericides/disinfectants (preferably 0.01-10% in the oral care layer); antibiotics (preferably 0.001-10% in the oral care layer); antifungals (preferably 0.1-10% in the oral care layer); tooth desensitizing agents (preferably 0.1-10% in the oral care layer); fluoride anticavity/antidecay agents (preferably 50 ppm to 10,000 ppm in the oral care layer); anti-tartar/anti-calculus agents; enzymes which inhibit the formation of plaque, calculus or dental caries; and nutritional supplements for local delivery to the teeth and surrounding tissue.

Suitable non-steroidal anti-inflammatory/analgesic agents include acetaminophen; methyl salicylate; monoglycol salicylate; aspirin; mefenamic acid; flufenamic acid; indomethacin; diclofenac; alclofenac; diclofenac sodium; ibuprofen; flurbiprofen; fentizac; bufexamac; piroxicam; phenylbutazone; oxyphenbutazone; clofezone; pentazocine; mepirizole; and tiaramide hydrochloride.

Suitable steroidal anti-inflammatory agents include hydrocortisone; prednisolone; dexamethasone; triamcinolone acetonide; fluocinolone acetonide; hydrocortisone acetate; prednisolone acetate; methylprednisolone; dexamethasone acetate; betamethasone; betamethasone valerate; flumetasone; fluorometholone; budesonide; and beclomethasone dipropionate.

Suitable local anesthetics include dibucaine hydrochloride; dibucaine; lidocaine hydrochloride; lidocaine; benzocaine; p-buthylaminobenzoic acid 2-(diethylamino) ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Suitable bactericides/disinfectants include thimerosol; phenol; thymol; benzalkonium chloride; benzethonium chloride; chlorhexidine; providone iodide; cetylpyridinium chloride; eugenol, and trimethylammonium bromide.

Suitable antibiotics include penicillin; meticillin; oxacillin; cefalotin; cefaloridin; erythromycin; lincomycin; tetracycline; chlortetracycline; oxytetracycline; metacycline; chloramphenicol; kanamycin; streptomycin; gentamicin; bacitracin; and cycloserine.

Suitable antifungal drugs include amphotericin; clotrimazole; econazole nitrate; fluconazole; griseofulvin; itraconazole; ketoconazole; miconazole; nystatin; terbinafine hydrochloride; undecenoic acid; and zinc undecenoate.

Suitable tooth-desensitizing agents include potassium nitrate and strontium chloride.

Suitable fluoride anticavity/antidecay agents include sodium fluoride, potassium fluoride and ammonium fluoride.

Suitable anti-tartar/anti-calculus agents include phosphates such as pyrophosphates, polyphosphates, polyphosphonates (e.g., ethane-1-hydroxy-1,1-diphosphonate, 1-azacycloheptane-1,1-diphosphonate, and linear alkyl diphosphonates), and salts thereof; linear carboxylic acids; and sodium zinc citrate; and mixtures thereof. Preferred pyrophosphate salts are the dialkali metal pyrophosphate salts, tetra-alkali metal pyrophosphate salts; and the hydrated or unhydrated forms of disodium dihydrogen pyrophosphate ($Na_2H_2P_2O_7$), tetrasodium pyrophosphate ($Na_4P_2O_7$), and tetrapotassium pyrophosphate ($K_4P_2O_7$). The pyrophosphate salts are described in more detail in Kirk & Othmer, Encyclopedia of Clinical Technology Third Edition, Volume 17, Wiley-Interscience Publishers (1982), the entire disclosure of which is herein incorporated by reference in its entirety.

Suitable enzymes that inhibit the formation of plaque, calculus or dental caries include: proteases that break down salivary proteins which are absorbed onto the tooth surface and form the pellicle, or first layer of plaque; lipases that destroy bacteria by lysing proteins and lipids that form the structural component of bacterial cell walls and membranes; dextranases, glucanohydrolases, endoglycosidases, and mucinases that break down the bacterial skeletal structure that forms a matrix for bacterial adhesion to the tooth; and amylases that prevent the development of calculus by breaking-up the carbohydrate-protein complex that binds calcium. Preferred enzymes include any of the commercially available proteases; dextranases; glucanohydrolases; endoglycosidases; amylases; mutanases; lipases; mucinases; and compatible mixtures thereof.

Suitable nutritional supplements for local delivery to the teeth and surrounding tissue include vitamins (e.g., vitamins C and D, thiamine, riboflavin, calcium pantothenate, niacin, folic acid, nicotinamide, pyridoxine, cyanocobalamin, para-aminobenzoic acid, and bioflavonoids); and minerals (e.g., calcium, phosphorus, fluoride, zinc, manganese, and potassium); and mixtures thereof. Vitamins and minerals useful in the present invention are disclosed in *Drug Facts and Comparisons* (loose leaf drug information service), Wolters Kluer Company, St. Louis, Mo., 1997, pp 3-17; the entire disclosure of which is herein incorporated by reference.

The oral care agent can also be any cosmetically active agent. As used herein, a "cosmetically active agent" includes any substance that can be released from the oral care layer to effect a desired change in the appearance of the teeth or surrounding tissue, or which imparts a socially desirable characteristic to the user, such as fresh breath. For example, a cosmetically active agent can be a breath freshener or an agent which effects whitening or bleaching of the teeth. Recognizing that in some cultures or in certain segments of Western society coloration of the teeth may be significant or desirable, the cosmetically active agent can also be any agent which imparts a color or tint to the teeth.

Suitable tooth whitening agents include peroxides, metal chlorites, perborates, percarbonates, peroxyacids, and combinations thereof. Suitable peroxide compounds include hydrogen peroxide, calcium peroxide, carbamide peroxide, and mixtures thereof. The preferred peroxides are hydrogen and carbamide peroxide. Suitable metal chlorites include calcium chlorite, barium chlorite, magnesium chlorite, lithium chlorite, sodium chlorite, and potassium chlorite; hypochlorite and chlorine dioxide. The preferred chlorite is sodium chlorite.

The preferred concentration of tooth whitening agent in the oral care layer of from about 0.01% to about 40%. If a peroxide compound is chosen as the tooth whitening agent, the peroxide compound should be equivalent to about 0.1% to about 20% of hydrogen peroxide, preferably from about 0.5% to about 13% of hydrogen peroxide, and most preferably from about 1% to about 10% of hydrogen peroxide, for example 9% of hydrogen peroxide.

As used herein, a "hydrogen peroxide equivalent" is the amount of peroxide compound necessary to deliver the same amount of hydroxyl radicals as a given amount of hydrogen peroxide. For example, it takes 3 moles of carbamide peroxide to deliver the same number of hydroxyl radicals as 1 mole of hydrogen peroxide. Therefore, to deliver the hydrogen peroxide equivalents disclosed in the preceding paragraph, carbamide peroxide should generally be present in an amount of from about 0.3% to about 60% and preferably from about 1.5% to about 39%, particularly preferably from about 3% to about 30%, for example 27%, in the oral care layer.

If hydrogen peroxide is used in the oral care layer, it is preferably from about 0.1% to about 30% by weight of the oral care layer. More preferably the amount of hydrogen peroxide in the oral care layer is from about 3% to about 20%. Most preferably the amount of hydrogen peroxide in the oral care layer is from about 6% to about 12%.

The oral care layer can also comprise additional ingredients which do not alter the adhesive, cohesive or structural properties of the layer, or interfere with the delivery of the oral care agent. Such additional ingredients include coloring compounds as described above; food additives; flavorants; sweeteners; and preservatives.

Any natural or synthetic flavorant or food additive, such as those described in Chemicals Used in Food Processing, Pub. No. 1274, National Academy of Sciences, pages 63-258 (the entire disclosure of which is herein incorporated by reference) can be used. Suitable flavorants include wintergreen, peppermint, spearmint, menthol, fruit flavors, vanilla, cinnamon, spices, flavor oils and oleoresins, as known in the art. The amount of flavorant employed is normally a matter of preference, subject to such factors as flavor type, individual flavor, and strength desired. Preferably, the oral care layer comprises from about 0.1% to about 5% flavorant.

Sweeteners useful in the present invention include sucrose, fructose, aspartame, xylitol and saccharine. The choice of sweeteners and the desired "sweetness" dictates the amount of sweetener to be added to the oral care layer. Preferably, the oral care layer comprises sweeteners in an amount from about 0.001% to about 5.0%.

The device of the invention is preferably substantially non-flat as provided to the user. As used herein, "substantially non-flat" means that the device is bent, creased or curved along its long axis. For example, the device may have a "J", "reversed J", "V", "U", or "C" shape or the like when viewed in cross-section. The oral care layer is located to the inside of the bend or curve (e.g., the concave side), so that the oral care layer is protected from inadvertent contact by the user. In normal use and handling, the user should only touch the backing layer, which forms the outside of the device. In the preferred embodiment, a user simple slides the substantially non-flat device onto the teeth and presses the device onto the teeth so that the oral care layer contacts at least the front portion of the teeth.

In addition, the oral care layer can be protected with an optional release liner, or a covering enclosing the inside (e.g., the concave side) of device. The release liner may be formed from any material which exhibits less affinity for the oral care substance than the oral care substance exhibits for itself and for the release liner material. The release liner preferably comprises a rigid sheet of material such as polyethylene, paper, polyester, or other material which is then coated with a non-stick type material. The release liner material can be coated with wax, silicone, teflon, fluoropolymers, or other non-stick type materials. A preferred release liner is Scotchpak® produced by 3M. The release liner may be cut to substantially the same size and shape as the oral care layer surface of the device, or the release liner may be cut larger than the oral care layer surface of the device to provide a readily accessible means for separating the material from the strip. The release liner may be formed from a brittle material which cracks when the device is flexed, from multiple pieces of material, or from a scored piece of material. Alternatively, the release liner can comprise two overlapping pieces, such as a typical adhesive strip bandage design. In one embodiment, the optional release liner can be integral with a package enclosing the device. A further description of materials suitable for use as a release liner is found in *Kirk-Othmer Encyclopedia of Chemical Technology*, Fourth Edition, Volume 21, pp. 207-218, the entire disclosure of which is incorporated herein by reference. The covering enclosing the inside (e.g., the concave side) of the present device can be made of similar materials.

In addition to the curve, crease or bend which may be possessed by the device of the invention when viewed in cross section, the device is of an overall size and shape to fit over some or all of the teeth in either the upper or lower dental arch of the user's mouth. Although the present device can be used on primary, mixed or permanent dentition, for ease of reference the invention will be discussed in terms of the permanent dentition of an average adult human being.

An adult human user will typically have a permanent dentition composed of sixteen teeth in the upper dental arch, and sixteen teeth in the lower dental arch. As used herein, "dental arch" means an individual row of teeth forming a tooth row attached to either the upper or lower jaw bone. The curve of the dental arch is known as the catenary arch. Each dental arch has the following tooth types arranged symmetrically in the arch: four incisors or front teeth, two canines, four bicuspids and six molars. The incisors and canines are called the anterior teeth, and the bicuspids and molars are called the posterior teeth. The shape of the anterior teeth is generally the same for the upper and lower dental arch, with the top set generally being larger. The posterior teeth are of generally the same size and shape in both the upper and lower dental arches.

Preferably, the device is of sufficient length to cover at least the facial surface of the anterior teeth in a dental arch, and is of sufficient width to extend from the facial surface of the teeth, over the crowns, and at least partially cover the lingual surface of the teeth. Generally, the device will begin coverage of the facial surface of the teeth at the point where the facial surface contacts the gums. It is understood that the device may partially cover the gums or other surrounding tissue. As used herein, the "facial" surface of a tooth is the surface toward the cheeks or lips, and the "lingual" surface of a tooth is the surface toward the tongue.

In a more preferred embodiment, the device is of sufficient length and width to cover the facial surface, crowns and at least partially cover the lingual surface of the anterior teeth in a dental arch. Particularly preferred is a device having sufficient length and width to cover the facial surface, crowns and at least partially cover the lingual surface of the anterior and at least a portion of the posterior teeth in a dental arch.

For a device designed to fit the upper dental arch, a suitable length is from about 7 cm to about 9 cm, and a suitable average width is from about 0.8 cm to about 2.5 cm. For a device designed to fit the lower dental arch, a suitable length is from about 4 cm to about 6 cm, and a suitable average width is from about 1 cm to about 2 cm. It is understood that the device is intended to fit a range of similarly-sized dental arches, and that the device, as used, is conformed to fit the dental arch of a particular user. Therefore, the dimensions presented herein are not intended to be limiting, but are rather presented as a guide for constructing the device. For example, devices designed for use in children or smaller adults are proportionally smaller than those described above for the normal-sized adult.

The device can be essentially any shape which allows sufficient coverage of the teeth, as discussed above. For example, when viewed in plan view, the device can be straight, or can be slightly bent; e.g., in conformity with the catenary arch of the upper or lower human dental arch. Where the device is designed to fit over all the teeth in a dental arch, the device is preferably bent into a horseshoe-shape that generally matches the catenary arch.

In flattened form and viewed in plan view, the device can be substantially rectangular in shape; e.g., having four edges which each pair of non-intersecting edges are close to parallel or are arched in the same way. For example, a device in which the "front" edge of the device and the "back" edge of the device are curved in the same way, and the side edges are essentially parallel or slightly off-parallel, is considered to be rectangular in shape; see, e.g., FIG. 12. As used herein, the "front" edge of the device is the long edge of that portion of the device placed against the facial surface of the teeth. As used herein, the "back" edge of the device is the long edge of that portion of the device placed against the lingual surface of the teeth. The "side" edges are the remaining edges of the device. The front and back edges are non-intersecting, and the "side" edges of the device are non-intersecting. The intersecting edges (e.g., a side edge and the front edge) do not have to intersect at exactly a right angle to be considered rectangular. Rather, the corner angle can be approximately 90'. Moreover, the corners formed by the intersecting edges can be rounded and still considered rectangular.

The device can also be substantially trapezoidal in shape when in flattened form and viewed in plan view. As used herein, "trapezoidal in shape" means any shape having four edges where the front and back edges are generally parallel or arched the same way, and the back edge is shorter than the front edge. The side edges are generally not parallel. For example, the device may be trapezoidal in shape when the front edge is convex and the back edge is concave and is also shorter than the front edge, and the side edges are not parallel; see, e.g., FIG. 13. The trapezoidal shape may help to reduce bunching or buckling of the device when placed on the dental arch, and allow the oral care layer more efficiently contact the surfaces of the teeth.

Alternatively, the shape of the device when in flattened form and viewed in plan view can be generally round, oval, or polygonal. It is understood that the shape of the device, when in flattened form and viewed in plan, does not have to be symmetrical. Moreover, the edges of the device need not be straight, but can be irregular.

Any or all of the edges of the device may be notched. By notched it is meant that there are one or more recesses, indentations, or curves of some type cut out of the device edge. The notches help prevent buckling of the device when the device is formed over the curve of the dental arch, and may be advantageously placed in the back edge of the device. In a preferred embodiment, the back edge of the device contains a plurality of notches substantially evenly spaced along the back edge.

Certain embodiments of the device will now be illustrated with reference to the figures, where like reference numbers indicated like structures.

Figure 2:
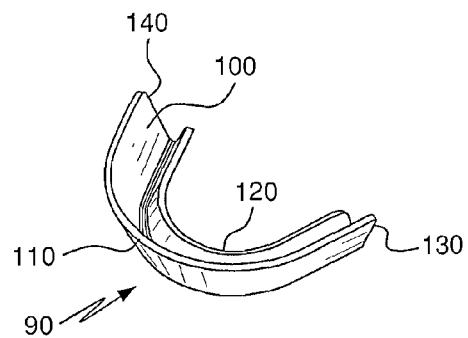
FIG. 2 is an isometric view of the device of FIG. 1 as seen from the front.

FIGS. 1 and 2 show back isometric and front isometric views, respectively, of an oral care delivery device of the invention generally designated as 90, which is designed to fit the upper dental arch. The device is bent into a horseshoe-shape that generally conforms to the catenary arch of a user. The inside 100 of the device, which is bounded by front edge 110, back edge 120, left side edge 130 and right side edge 140, contains the oral care layer.

Figure 3:
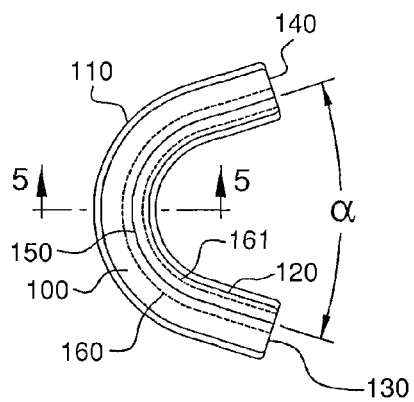
FIG. 3 is a top plan view of the of the device of FIG. 1.

FIG. 3 shows a top plan view of the device of FIGS. 1 and 2. Line 5-5 in FIG. 3 bisects the device along a line corresponding to the medial line of a dental arch, and defines the two arms of the horseshoe. The horseshoe arms are set at angle α of approximately 36°, generally corresponding to the angle of a user's teeth in the catenary arch. Main fold line 150 and secondary fold lines 160 and 161 extend from left side edge 130 to right side edge 140 along the long axis of the device. Generally, the fold lines are formed when the device is pressed or vacuum formed into a forming die during the folding process. Preferably, the fold lines correspond merely to the area of the device which is folded, and not a structural characteristic that necessitates the fold. However, to necessitate the fold, the area of the dental wax corresponding to the fold lines can be weakened, scored, etched, gouged, or impressed by stamping or other similar mechanical means.

Figure 4:
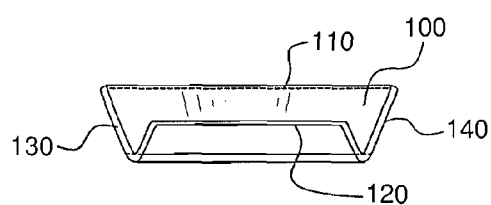
FIG. 4 is a back view of the device of FIG. 1.

The device is folded along the main and secondary fold lines, with the oral care layer to the inside 100 of the device, and the backing layer to the outside. The main fold line 150 and secondary fold lines 160 and 161 are offset towards back edge 120 of the device. Folding of the device along the offset fold lines provides a portion of the inside of the device from the front edge to the fold lines which is larger than the portion of the device from the back edge to the fold lines. This larger portion is intended to contact the facial surface of the teeth when the device is placed over the dental arch. As used herein, an "axis" of the device includes both linear and curvilinear lines running from side edge to side edge of the device. FIG. 4 is a back view of the device of FIGS. 1 and 2, showing how folding of the device along the offset main fold line 150 and secondary fold lines 160 and 161 divides the device into larger and smaller portions as described above.

Figure 5:
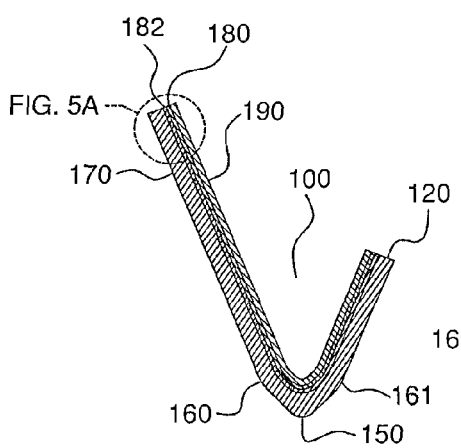
FIG. 5 is a cross-sectional view taken along line 5-5 of FIG. 3.

FIG. 5 is a cross-sectional view of the device 90 of FIGS. 1 and 2 along line 5-5 of FIG. 3, showing the arrangement of the oral care layer 190, the first part of the non-woven binding material 180 substantially invested in the oral care layer 190, the second part of the non-woven binding material 182 substantially invested in the backing layer 170, and the backing layer 170. The device is bent along main fold line 150 and secondary fold lines 160 and 161 into a "reversed J" shape, so that the oral care layer 190 is located to the inside 100 of the device. The long arm of the "reversed J" ends in the front edge 110.

Figure 5A:
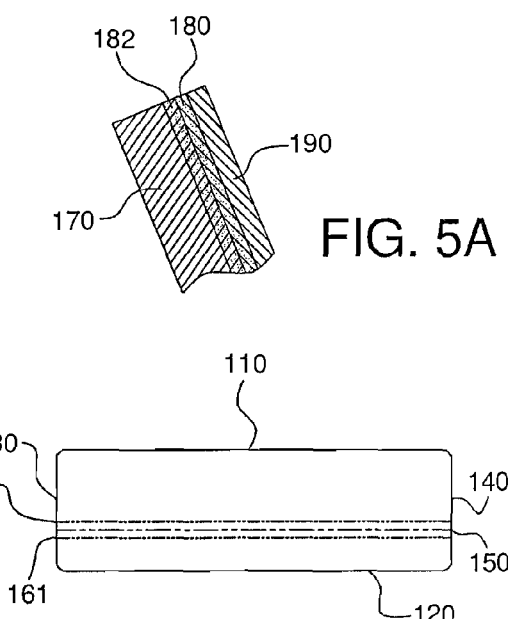
FIG. 5A is an exaggerated view of a portion of the cross-section of FIG. 5.

FIG. 5A is a blow-up of a portion of the cross-section view of FIG. 5, further illustrating the arrangement of the oral care layer 190, the first part of the non-woven binding material 180 substantially invested in the oral care layer 190, the second part of the non-woven binding material 182 substantially invested in the backing layer 170, and the backing layer 170.

Figure 6:
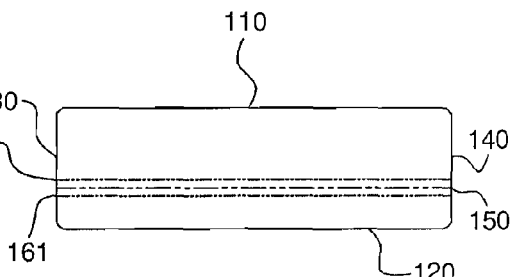
FIG. 6 is a top plan view of a flattened form of the device of FIG. 1.

FIG. 6 is a top plan view of the device of FIGS. 1 and 2 shown in flattened form to illustrate the rectangular shape of the unfolded device. Front edge 110 and back edge 120 are non-intersecting, and left side edge 130 and right side edge 140 are non-intersecting. Main fold line 150 and secondary fold lines 160 and 161 are located approximately ⅓ the distance from front edge 110 to back edge 120.

Figure 7:
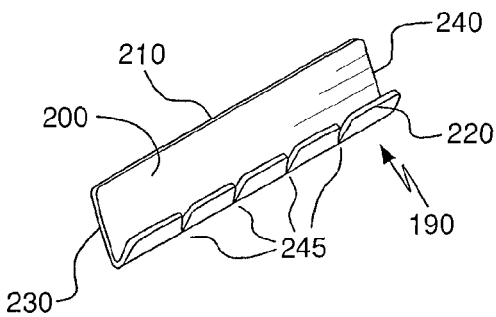
FIG. 7 is an isometric view of another embodiment of a device of the invention as seen from the back.

FIG. 7 is a back isometric view of another oral care delivery device of the invention generally designated 190, which is designed for placement over either the upper or lower dental arch. The inside 200 of the device, which is bounded by front edge 210, back edge 220, left side edge 230 and right side edge 240, contains the oral care layer. A plurality of notches 245 are spaced essentially evenly along the back edge 210 of the device. As described above, the notches help prevent buckling of the device when the device is manipulated to conform to the curve of the dental arch. The device is substantially straight, and is molded to fit the curvature of the catenary arch during placement in the user's mouth.

Figure 8:
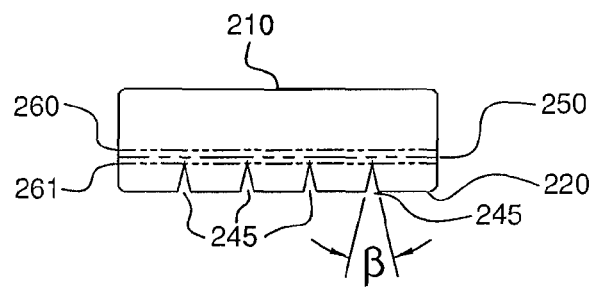
FIG. 8 is top plan view of a flattened form of the device of FIG. 7.

FIG. 8 shows the device 190 of FIG. 7 in flattened form to illustrate the rectangular shape of the unfolded device, and the positioning of notches 245. The device has a main fold line 250 and secondary fold lines 260 and 261 offset from front edge 210 as in the previous embodiment, located approximately ⅓ the distance from front edge 210 to back edge 220. The notches 245 extend from back edge 210 to the secondary fold 230 line closest to the back edge, with the apex of the notches contacting the secondary fold line. The sides of each notch form an angle β of approximately 28°.

Figure 9:
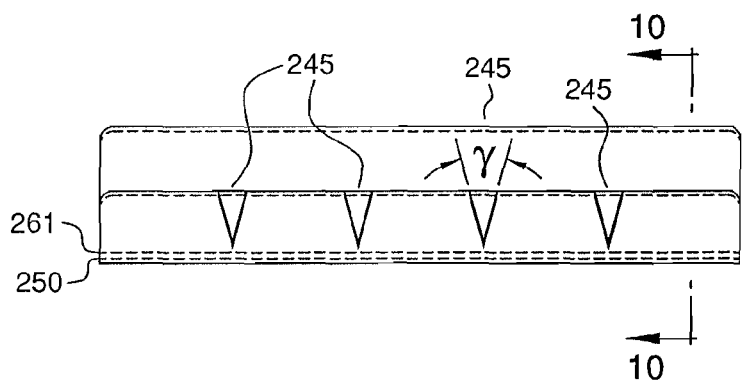
FIG. 9 is a back view of the device of FIG. 7.

FIG. 9 is a back view of the device 190 of FIG. 7, showing how folding of the device along the offset main fold line 250 and secondary fold lines 260 and 261 provides a portion of the device from the front edge to the fold lines which is larger than the portion from the back edge to the fold lines. The larger portion contacts with the facial surface of the teeth when the device is placed over the dental arch. The notches 245 are contained within the portion of the device which contacts the lingual surface of the teeth when placed over the dental arch. The sides of each notch form an angle γ of approximately 28°.

Figure 10:
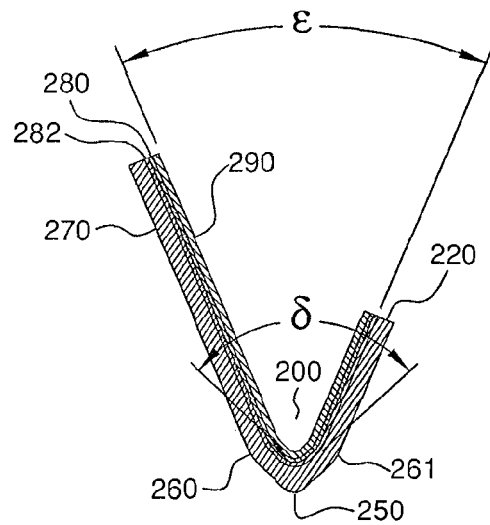
FIG. 10 is a cross-sectional view taken along line 10-10 of FIG. 9.

FIG. 10 is a cross-sectional view of the device 190 of FIG. 7 taken along line 10-10 of FIG. 9, showing the arrangement of an oral care layer 290, a first part of the non-woven binding material 280 substantially invested in the oral care layer 290, a second part of the non-woven binding material 282 substantially invested in a backing layer 270, and the backing layer 270. The device is bent along main fold line 250 and secondary fold lines 260 and 261 into a "reversed J" shape, so that the oral care layer 290 is located to the inside 200 of the device. The long arm of the "reversed J" ends in the front edge 210. The surface of oral care layer 290 between the secondary fold lines 260 and 261 is bent into an angle δ of approximately 90° by folding the device along the main fold line 250. The surface of the oral care layer 290 between front edge 210 and the secondary fold line 260, and the surface of the oral care layer 290 between the back edge 220 and the secondary fold line 261, are bent into an angle ε of approximately 45° relative to each other by folding the device along each secondary fold line.

Figure 11:
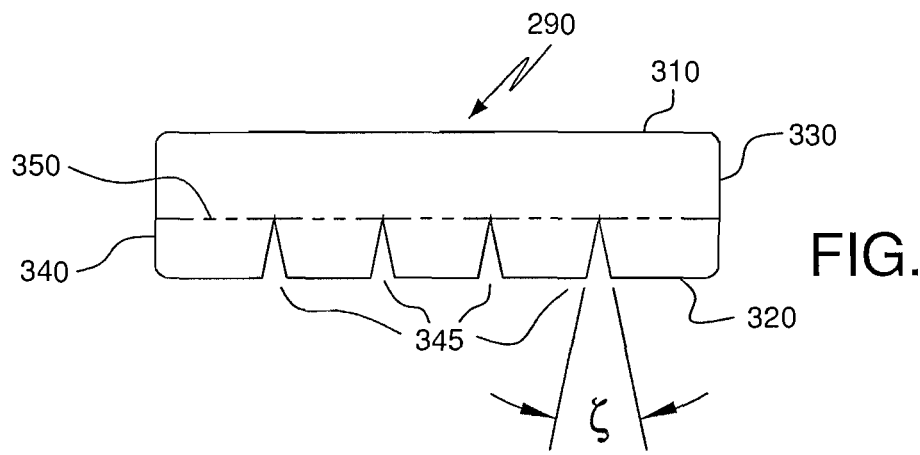
FIG. 11 is a top plan view of a flattened form of a further embodiment of a device of the invention.

FIG. 11 is a top plan view of a further oral care delivery device of the invention generally designated 290, which is designed to fit the upper dental arch of a user. The device is shown in flattened form to illustrate the rectangular shape. The rectangle is defined by front edge 310 and back edge 320, and side edges 330 and 340. The device has a single fold line 350 which is slightly offset from the center axis of the device toward the back edge 320. A plurality of substantially evenly spaced notches 345 are cut into back edge 320. The sides of each notch 345 form an angle ζ of approximately 22°, and the apex of each notch contacts fold line 350.

Figure 12:
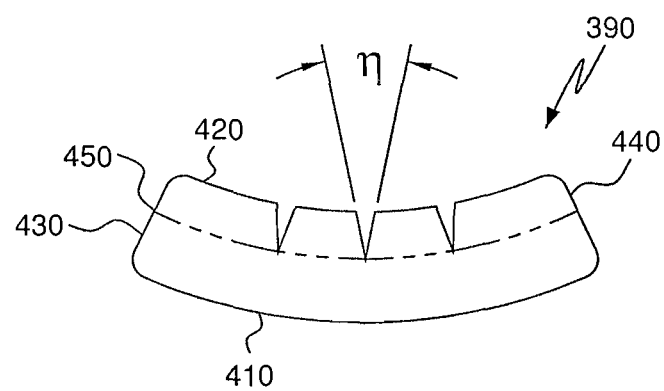
FIG. 12 is a top plan view of a flattened form of a further embodiment of a device of the invention.

FIG. 12 is a top plan view of another oral care delivery device of the invention generally designated 390, which is designed to fit the upper dental arch of a user. The device is shown in flattened form to illustrate the rectangular shape. The rectangle is defined by front edge 410 and back edge 420, and side edges 430 and 440. Front edge 410 and back edge 420 are curved in the same way and side edges 430 and 440 are slightly off-parallel. The device has a single fold line 450 which is slightly offset from the center axis of the device toward the back edge. A plurality of substantially evenly spaced notches 445 are cut into back edge 420. The sides of each notch 445 form an angle η of approximately 22°, and the apex of each notch contacts fold line 450.

Figure 13:
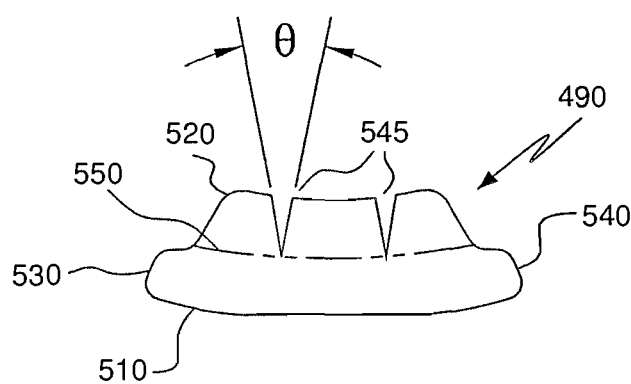
FIG. 13 is a top plan view of a flattened form of a further embodiment of a device of the invention.

FIG. 13 is a top plan view of a further oral care delivery device of the invention generally designated 490, which is designed to fit the lower dental arch of a user. The device is shown in flattened form to illustrate the essentially trapezoidal shape. The trapezoid is defined by front edge 510 and back edge 520, and side edges 530 and 540. Front edge 510 and back edge 520 are slightly curved, and back edge 520 is shorter in length than front edge 510. Side edges 530 and 540 are not straight, but follow an irregular course which forms protrusions on either side of the flattened pattern. When the device is folded and placed over the dental arch, the protrusions ensure that at least the facial surface of the incisors are in contact with the oral care layer. The device has a single fold line 550 which is slightly offset from the center of the device toward the back edge 520. A plurality of substantially evenly spaced notches 545 are cut into back edge 520. The sides of each notch 545 form an angle θ of approximately 22°, and the apex of each notch contacts fold line 550.

The device can be constructed using techniques well known in the art. For example, the components comprising the backing layer can be mixed, melted and extruded in a continuous or discontinuous layer of a desired thickness, which can be cut to the appropriate size and shape. Alternatively, the backing layer can be produced by pressing the mixed, melted components into a flat sheet of a desired thickness, which is then cut to the appropriate size and shape. The binding material can be invested in the backing layer by techniques well known in the art, such as lamination, hot-melt extrusion, and the like, or the two layers can be coextruded.

Likewise, the oral care layer can be prepared using polymer synthesis and formulation techniques known in the art (see, e.g., U.S. Pat. No. 4,581,821 of Cahalan et al., supra, and U.S. Pat. No. 6,576,712 of Feldstein et al., supra), and formed into a layer of a desired thickness suitable for investment by a first part of the binding material. For example, the polymers, plasticizers oral care agent and any other components comprising the oral care layer can be melted in a hotmelt mixer and extruded as a sheet between two release liners, or can be casted. The oral care layer can be removed from between the release liners and integrated with the binding material; e.g., by lamination. Alternatively, the oral care layer can be extruded directly onto the binding material.

In one embodiment, an oral care agent, for example a hydrogen or carbamide peroxide, can be placed (e.g., by printing) on top of a first part of the non-woven binding material, the second part of which has been substantially invested into a backing layer. A melted mixture comprising all the components of an oral care layer except the oral care agent is then extruded directly on top of the oral care agent. The components of the oral care layer flow into and around the openings in the binding material such that the pore space of the binding material is fully encompassed by the oral care agent and such that the oral care agent contacts the backing layer. As the melted oral care layer components solidify, the oral care agent is drawn into and distributed throughout the oral care layer.

Optionally, a scrim can be placed over the oral care agent which has been placed on top of the binding material, prior to extrusion of the oral care layer. The melted mixture comprising the remaining oral care layer components is then extruded onto the scrim, where it flows into and around the openings in the scrim so that the scrim is entirely surrounded by the melted oral care layer material. As the oral care layer solidifies, it absorbs the oral care agent as described above, and also entraps the scrim so that the scrim is embedded in the oral care layer.

Specific processes for constructing the devices of the invention are given in the Examples below.

Preferably, the device of the invention is provided to the user substantially ready for placement on the teeth. That is, the device will preferably be provided in substantially non-flat form, and all the user need do is conform the device onto the upper or lower dental arch with normal manual pressure.

In practice, the user wets the device before placement in the mouth, e.g., with water or saliva. Alternatively, the user can wet the surface of the teeth to be treated; e.g., with water or saliva, before placement of the device in the mouth. Wetting the device causes the hydrophilic polymer in the oral care layer to begin to swell, which in turn may enhance the adhesive properties of the layer and/or activate the oral care agent. Swelling of the hydrophilic polymer can also cause the oral care layer to fill in the cracks or irregularities found in the surface of the teeth and surrounding tissue, so that maximum contact is made with these surfaces.

The device is then placed over the teeth to be treated, and formed around the teeth and surrounding tissue with manual pressure. The device should be conformed to the teeth so that the oral care layer is substantially entirely in contact with at least the facial surfaces and the crowns of the teeth to be treated. Depending on the size of that portion of the device in contact with the lingual surface of the teeth to be treated, the lingual surface of the teeth may only be partially covered.

Once formed around the teeth and surrounding tissue, the device is left in place for a sufficient time to produce the desired effect. The length of time that the device should be left in place varies with the type of treatment to be performed, the severity of the condition, the age and health of the user, and the like. The length of time which the device is left on the teeth can therefore be varied in order to achieve a desired result. For both therapeutic and cosmetic applications, the device can be left in place, for example, for about 15 minutes to about 4 hours per treatment, preferably for about 30 minutes to about 1 hour per treatment. Longer and shorter treatment times are contemplated.

For embodiments of the invention which employ an oral care layer capable of sustained release of the oral care agent, treatment times can be substantially less than treatment times normally recommended for prior delivery systems. For example, treatment times of about 15 to about 30 minutes with a device of the invention employing a sustained release layer can produce results comparable to or better than those achieved with prior delivery systems using longer treatment times. Once a single treatment has been completed, the device is simply removed from the teeth by the user and discarded.

The frequency and total number of therapeutic or cosmetic treatments also depend on factors such as the type of treatment to be performed, the severity of the condition, the age and health of the user, and the like. The frequency and total number of treatments with the present device can therefore be varied in order to achieve a desired result. For therapeutic and cosmetic applications, the device can be applied to the teeth once or twice a day for 1 to 28 days, with the treatment regimen being repeated in 4 to 6 months from the last treatment. The preferred regimen is once a day for 3 days or 5 days.

For embodiments of the invention which employ an oral care layer capable of sustained release of the oral care agent, the frequency and total number of treatments can be substantially less than those recommended for prior delivery systems. For example, a device employing a sustained release oral care layer can be used once a day for 4 days to 2 weeks, with results comparable to or better than those achieved with prior delivery systems.

A preferred use of the device of the invention is to deliver a tooth whitening agent to the teeth. In practice, a device comprising an oral care layer which comprises a tooth whitening agent is provided to the use and is used as described above. Preferably, wetting the device activates the tooth whitening agent.

The device is left in place for a sufficient time to produce the desired effect. The length of time that the device should be left in place varies with the extent of the tooth discoloration or staining, the degree of whitening desired by the user, and the like. The length of time which the device is left on the teeth can therefore be varied in order to achieve a desired result. Generally, the device can be left in place for about 15 minutes to about 2 hours per treatment, preferably for about 30 minutes to about 1 hour per treatment. Longer and shorter treatment times are contemplated. A preferred treatment time is approximately 1 hour.

In a preferred embodiment, the device comprises an oral care layer capable of sustained release of the tooth whitening agent. In particular, the oral care layer can comprise a PEG-PVP-based pressure sensitive adhesive as disclosed in U.S. Pat. No. 6,576,712 of Feldstein et al, supra. Use of sustained-release oral care layers can significantly reduce treatment times as compared to the treatment times normally recommended for prior tooth whitening systems.

After a single treatment has been completed, the device is removed from the teeth by the user and discarded. The treatment is preferably repeated once a day (using a fresh device for each treatment) for one to two weeks. More preferably, the tooth whitening treatment is repeated once a day for 4 to 7 days. The tooth whitening treatment regimen can be repeated after, for example, 4 to 6 months, depending on the extent to which tooth discoloration or staining occurs during this period.

The device of the invention can be packaged by any means suitable for containing and transporting the devices to the consumer. Preferably, the device is placed in a hermetically sealed, single use pouch. Preferably, these pouches are made of silicone or fluorocarbon coated foil, Mylar, or wax coated foil to protect the device. The device can be sealed within the pouch under full or partial vacuum. A preferred pouch design is of the "peel-n-seal" type, wherein the user is presented with the device upon opening the pouch. The user may then grasp the device only by the backing layer, thus minimizing the chance of damaging or contaminating the oral care layer.

It is contemplated that a plurality of devices in single use packages can be packaged together. For example, a number of devices in single use packages equal to the recommended number of treatments for a given treatment regimen can be provided to the consumer in a larger package.

The invention will now be illustrated with the following non-limiting example.

EXAMPLE 1

Construction of a Device for Delivering a Tooth Whitening Agent

A delivery system for delivering a tooth whitening agent according to the present invention was constructed as follows.

TABLE 3

Backing Layer Formulation

| Item | Brand Name | Supplier | Percentage |
|---|---|---|---|
| Microcrystalline Wax | Microcrystalline 180/185 | Koster Keunen Inc. | 50% |
| Paraffin Wax | Paraffin 140/145 | Koster Keunen Inc. | 15% |
| Hydrocarbon Resin | Escorez 5380 | ExxonMobil Chemical | 35% |

The backing layer was prepared as follows. The microcrystalline wax, paraffin, and Escorez 5380 were weighed and transferred into a Qorpak® jar (Qorpak, Bridgeville, Pa.). The materials were heated to 85° C.-90° C. with stirring to obtain a clear liquid melt. The clear liquid melt was cooled to 65° C.-75° C. with stirring. At this temperature, the viscosity of the clear liquid melt was such that a Gardner's knife was used to make "draw-downs." A silicone-coated PET release liner (Rexam 92A; Rexam Coated Films & Papers, Charlotte, N.C.) was placed on a glass plate which had been heated to 38° C.-40° C. The clear liquid melt (at 65° C.-75° C.) was coated onto the release liner at a thickness of about 0.64 mm (25 mils) using a Gardner's knife. Immediately after drawing down the clear liquid melt onto the release liner, the release liner with the clear liquid melt was removed from the warm glass plate and was cooled to room-temperature. The clear liquid melt was solidified to form the backing layer. The target thickness for the backing layer was about 0.38 mm (15±2 mils). It is contemplated that this process could also produce backing layers having a thickness of from about 0.025 mm (1 mil) to about 0.508 mm (20 mils).

Non-woven binding material—The binding material was composed of a layer of spun bonded polypropylene (Typar®). The target thickness of the binding layer was about 0.152 mm (6 mils±1 mil). The binding material was invested in the backing layer as follows. The solidified backing layer on the release liner produced above was placed, release liner-side down, on a glass plate and heated to 65°-70° C. The binding material was placed on the backing layer, and a second release liner was placed on the binding material, with the siliconized side of the release liner facing the binding material. A roller was passed over the second release liner pressing the binding material into the warm wax of the backing layer. The resultant set (first release liner/backing layer/binding material/second release liner) was cooled to room temperature to form a composition wherein a second part of the binding material was substantially invested in the backing layer.

TABLE 4

Oral Care Layer Formulation

| Item | Brand Name | Supplier | Percentage |
| --- | --- | --- | --- |
| Polyvinylpyrrolidone K90 (PVP90) | Kollidone 90 | BASF | 58% |
| Polyethylene Glycol 400 | Carbowax Polyethylene Glycol 400 | Union Carbide | 30% |
| Acrylic acid esters | Eudragit L 100/55 | Rohm America | 12% |

The oral care layer was produced as follows. The Kollidone 90 and Eudragit L100/55 powders were mixed and blended with the polyethylene glycol 400 ("PEG 400") using a hot-melt-mixing procedure at 140° C. in a standard hotmelt mixer-extruder. The blend was extruded at 140° C. through a slot die spaced at 0.25 mm (10 mils) width using a single screw extruder, to obtain a film of about 0.38 mm (15 mils) thick. The extrudate was collected on a siliconized release liner using standard post-extrusion collecting equipment.

The oral care agent (an aqueous hydrogen peroxide solution) was added to the oral care layer, and the oral care layer was laminated to the binding material, as follows. A 35-50% hydrogen peroxide solution was printed onto the binding material side of the backing layer/binding material composition in a controlled process, such that the amount of hydrogen peroxide solution printed onto the binding material was equivalent to 3-10% of oral care layer. The melted Kollidone 90-Eudragit L100/55-polyethylene glycol 400 blend was extruded on top of the hydrogen peroxide solution printed onto the binding material. The melted blend absorbed the hydrogen peroxide solution as it was cooled, and in the process adhered itself into and onto the binding material.

An optional scrim was embedded in the oral care layer as follows. DELNET® non-woven polyolefin fabric scrim (Del-Star Technologies, Inc., Middletown, Del.) was placed over the aqueous hydrogen peroxide solution which had been printed onto the non-woven. The melted Kollidone 90-Eudragit L100/55-polyethylene glycol 400 blend was extruded on top of the scrim. The melted blend flowed through and around the voids in the scrim, so that the scrim was entirely surrounded by the melted blend. Upon cooling and solidification of the melted blend, the scrim was embedded within the oral care layer. The melted blend also absorbed the hydrogen peroxide solution as it cooled, and in the process adhered itself to the binding material.

After the backing and oral care layers were formed with the binding material as described above, devices of the invention were cut to the desired size and shape and vacuum formed on a forming die. The overall thickness of the device was about 0.51 mm-0.61 mm (20-24 mils).

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:
1. A device for delivering an oral care agent to teeth, the device comprising:
a backing layer comprising a permanently deformable material;
an oral care layer separately constructed from the backing layer, and in contact with and adjacent the backing layer, the separately constructed backing layer and oral care layer joined via an adhesive bond where the backing layer and oral care layer engage one another, the oral care layer comprising a pressure-sensitive adhesive comprising at least one hydrophilic polymer, at least one water-soluble plasticizer that is miscible with the hydrophilic polymer and at least one oral care agent absorbed in the pressure sensitive adhesive; and
a binding material comprising a non-woven material, the binding material having a first part and a second part, the binding material aiding in the adhesive stability of the adhesive bond between the backing layer and the oral care layer, the binding material first part having a first surface;
wherein the second part of the binding material is fully invested in the backing layer, and the first part of the binding material is saturated with at least a portion of the oral care layer,
wherein the oral care layer penetrates below the first surface, of the binding material to form an oral care layer/binding material composition,
wherein a portion of the oral care layer is not invested in the binding material, the portion located above the first surface and immediately adjacent the oral care layer/binding material composition;
wherein the oral care layer has an adhesiveness when hydrated relative to the surface of the teeth of a subject that is sufficient to retain the device on the subject's teeth when placed thereon, and
wherein the oral care layer has a tack of greater than about 50 g/cm$^2$.
2. The device of claim 1, wherein the second part of the binding material is co-extensive with the backing layer.
3. The device of claim 1, wherein the length and width dimensions of the second part of the binding material are less than the length and width dimensions of the backing layer.
4. The device of claim 1 further comprising a plurality of notches, wherein said plurality of notches are substantially evenly spaced along a back edge.
5. The device of claim 4, wherein the notches form an angle of about 28°.

6. The device of claim 1, further comprising a fold line along the long axis of the device corresponding to an area of the device which is folded to divide the device into a lingual side and a facial side.

7. The device of claim 6, wherein the apex of the notches contact the fold line.

8. The device of claim 6, wherein the backing layer along the fold line is one or more of weakened, scored, etched, gouged, and impressed by stamping.

9. The device of claim 6, wherein the fold line is located about one third the distance from the front edge to a back edge.

10. The device of claim 6, wherein the device is folded along the fold line to have a "J", "reversed J", "V", "U", or "C" shape when viewed in cross-section.

11. The device of claim 1, wherein the backing layer comprises a wax, a resin, or mixtures thereof.

12. The device of claim 1, wherein the binding material is selected from a group consisting of a polyolefin; polyester; polyurethane; polyamide; polyaramide; and glass.

13. The device of claim 12, wherein the binding material comprises a polypropylene.

14. The device of claim 1, wherein the binding material is from about 0.089 mm to about 0.279 mm thick.

15. The device of claim 1, wherein the binding material has a thickness of about 0.114 mm to about 0.203 mm thick;
wherein the first part of the binding material comprises one half the thickness,
wherein the second part of the binding material comprises another one half the thickness.

16. The device of claim 1, wherein:
i) the backing layer consists of microcrystalline wax, paraffin wax; and hydrocarbon resin;
ii) the binding material consists of a spun bonded polypropylene; and
iii) the oral care layer consists essentially of hydrogen peroxide, polyvinylpyrrolidone K90, polyethylene glycol 400; and methacrylic acid-ethyl acrylate copolymer (1:1).

17. The device of claim 1, wherein the device is substantially non-flat and has a front edge running along the long axis of the device to be disposed along the facial side of the teeth and a back edge running along the long axis of the device to be disposed along the lingual side of the teeth.

18. The device of claim 1, wherein the back edge comprises a plurality of notches.

19. A device for delivering an oral care agent, wherein the device is sized to fit over a plurality of teeth in an upper or lower dental arch in a subject, the device comprising:
a permanently deformable backing layer;
a non-woven binding material comprising a first part and a second part; and
an oral care layer comprising a pressure-sensitive adhesive comprising at least one hydrophilic polymer, at least one water-soluble plasticizer that is miscible with the hydrophilic polymer and at least one oral care agent absorbed in the adhesive, wherein the first part of the binding material is substantially invested in at least a portion of the oral care layer, and the second part of the binding material is substantially invested in at least a portion of the backing layer, and
a scrim embedded in the oral care layer, the scrim located in the oral care layer not occupied by the first part of the binding material substantially invested in the oral care layer, the scrim having a melting temperature above a melting temperature of the oral care layer,
wherein the oral care layer has an adhesiveness when hydrated relative to the surface of the teeth of the subject that is sufficient to retain the device on the user's teeth when placed thereon.

20. A substantially non-flat device for delivering an oral care agent to a user's teeth, the device comprising:
a permanently deformable backing material having a facial portion and a lingual portion separated by a long axis of the device, the facial portion positioned on the lips side of the teeth and the lingual portion on the tongue side of the teeth when the device is placed on the teeth by the user, and a convex side that is in contact with the teeth when the device is placed on the teeth by the user;
a binding material having a first side and a second side, the first side of the binding material fully invested in the convex side of the facial portion of the backing material; and
an oral care substance saturating the second side of the binding material, the oral care substance comprising a pressure-sensitive adhesive comprising at least one hydrophilic polymer, at least one water-soluble plasticizer that is miscible with the hydrophilic polymer and an oral care agent absorbed in the adhesive;
wherein the oral care substance has an adhesiveness when hydrated relative to the surface of the teeth of a subject that is sufficient to retain the device on the subject's teeth when placed thereon;
wherein the oral care substance is separately constructed from the permanently deformable backing material, and in contact with and adjacent the backing material, the separately constructed backing material and oral care substance joined via an adhesive bond where the backing material and oral care substance engage one another,
wherein the binding material aids in the adhesive stability of the adhesive bond between the permanently deformable backing material and oral care substance, the binding material first side having a first surface;
wherein the oral care substance penetrates below the first surface to form an oral care substance/binding material composition,
wherein a portion of the oral care substance above the first surface is located immediately adjacent the oral care substance/binding material composition,
wherein the oral care substance has a tack greater than about 50 g/cm$^2$.

21. The device of claim 20 wherein the device comprises a "J", "reversed J", "V", "U", or "C" shape when viewed in cross-section.

22. The device of claim 20 wherein the user must exert a pressure of at least 100,000 Pascals for at least one second to deform the backing material.

23. The device of claim 20 further comprising a plurality of notches on the lingual portion of the backing material.

24. The device of claim 23 wherein the notches are evenly spaced.

25. The device of claim 23 wherein the sides of each notch forms an angle of about 28 degrees.

26. The device of claim 20 further comprising the first side of the binding material fully invested in the convex portion of the lingual side of the backing material.

27. The device of claim 20 wherein the device is curved along the long axis.

28. The device of claim 20 wherein the facial portion comprises about two-thirds of the device.

29. The device of claim 20 further comprising the first side of the binding material fully invested in the convex side of the lingual portion of the backing material.

30. The device of claim 27 further comprising the oral care substance saturating the second side of the binding material on the lingual portion of the backing material.

31. The device of claim 20 further comprising a release liner sized to cover the oral care substance, the release liner comprising a material that exhibits less affinity for the oral care substance than the oral care substance exhibits for itself.

32. The device of claim 31 wherein the release liner material is selected from a group consisting of polyethylene, paper, and polyester.

33. The device of claim 31 wherein the release liner comprises a rigid material having a convex shape corresponding to the convex shape of the device.

34. The device of claim 1, wherein the oral care layer is formed by melting and extruding a mixture comprising said hydrophilic polymer, water-soluble plasticizer and oral care agent to form said pressure-sensitive adhesive containing said oral care agent absorbed therein.

35. The device of claim 1, wherein the oral care layer is formed by melting and extruding a mixture comprising said hydrophilic polymer and water-soluble plasticizer, and absorbing said oral care agent into the extruded mixture to form said pressure-sensitive adhesive containing said oral care agent absorbed therein.

36. The device of claim 1, wherein the adhesiveness of the oral care layer with respect to the surface of the user's teeth is from about 200 N/m to about 400 N/m.

37. The device of claim 19, wherein the adhesiveness of the oral care layer with respect to the surface of the user's teeth is from about 200 N/m to about 400 N/m.

38. The device of claim 20, wherein the adhesiveness of the oral care layer with respect to the surface of the user's teeth is from about 200 N/m to about 400 N/m.

39. The device of claim 1, wherein the second part of the binding material comprises about one half of the binding material.

* * * * *